(12) United States Patent
Miller et al.

(10) Patent No.: US 10,398,445 B2
(45) Date of Patent: Sep. 3, 2019

(54) METHOD AND APPARATUS FOR CLAMPING TISSUE LAYERS AND OCCLUDING TUBULAR BODY STRUCTURES

(71) Applicant: Amsel Medical Corporation, Cambridge, MA (US)

(72) Inventors: Arnold Miller, Cambridge, MA (US); Raanan Miller, Cambridge, MA (US); Nir Lilach, Kfar Yehoshua (IL); William Edelman, Sharon, MA (US)

(73) Assignee: AMSEL MEDICAL CORPORATION, Cambridge, MA (US)

( * ) Notice: Subject to any disclaimer, the term of this patent is extended or adjusted under 35 U.S.C. 154(b) by 0 days.

(21) Appl. No.: 15/699,975

(22) Filed: Sep. 8, 2017

(65) Prior Publication Data
US 2018/0021044 A1    Jan. 25, 2018

Related U.S. Application Data

(63) Continuation of application No. 15/438,924, filed on Feb. 22, 2017, now abandoned, which is a
(Continued)

(51) Int. Cl.
*A61B 17/12* (2006.01)
*A61B 17/00* (2006.01)
(Continued)

(52) U.S. Cl.
CPC ...... *A61B 17/122* (2013.01); *A61B 17/12031* (2013.01); *A61B 17/1285* (2013.01);
(Continued)

(58) Field of Classification Search
CPC ............ A61B 17/0057; A61B 17/0644; A61B 17/12; A61B 17/12009; A61B 17/122;
(Continued)

(56) References Cited

U.S. PATENT DOCUMENTS

| | | |
|---|---|---|
| 3,971,284 A | 7/1976 | Hasson |
| 4,007,743 A | 2/1977 | Blake |

(Continued)

FOREIGN PATENT DOCUMENTS

| | | |
|---|---|---|
| EP | 1745750 | 1/2007 |
| EP | 1908419 A1 | 4/2008 |

(Continued)

OTHER PUBLICATIONS

EPO Communication in PCT US2015019001, dated Feb. 12, 2018.

*Primary Examiner* — Martin T Ton
(74) *Attorney, Agent, or Firm* — Bookstein IP Law

(57) ABSTRACT

Apparatus and methods for occluding hollow body structures, such as blood vessels, and for attaching tissue layers together by providing implantable elements on opposite sides of the structure or tissue layers and drawing the implants together to occlude the body structure and/or bring the tissue layers together. The implants are deliverable in a low profile configuration and self-expand to an enlarged configuration. The implantable elements are delivered by transfixing the body structure, then releasing the implants on opposite sides of the body structure and drawing the implants together to effect an occlusion or attachment. The implants are configured to apply oppositely directed forces to opposite surfaces of the tissue layers at alternate, circumferentially spaced locations and may constrain the tissue in a serpentine pattern or in a direct clamping pattern. The
(Continued)

implants grip the tissue in a manner that defines a pressure zone about the transfixion aperture that prevents leakage from the aperture.

13 Claims, 49 Drawing Sheets

Related U.S. Application Data continuation-in-part of application No. 14/639,814, filed on Mar. 5, 2015, now Pat. No. 9,936,955, and a continuation-in-part of application No. 14/272,304, filed on May 7, 2014, now Pat. No. 10,076,339, and a continuation-in-part of application No. 13/857,424, filed on Apr. 5, 2013, now abandoned, and a continuation-in-part of application No. 13/348,416, filed on Jan. 11, 2012, now abandoned.

(60) Provisional application No. 62/408,426, filed on Oct. 14, 2016, provisional application No. 62/084,989, filed on Nov. 26, 2014, provisional application No. 61/948,241, filed on Mar. 5, 2014, provisional application No. 61/820,589, filed on May 7, 2013, provisional application No. 61/431,609, filed on Jan. 11, 2011.

(51) Int. Cl.
   *A61B 17/128* (2006.01)
   *A61B 17/122* (2006.01)
   A61B 90/00 (2016.01)
   A61B 17/34 (2006.01)

(52) U.S. Cl.
   CPC ..... *A61B 17/12109* (2013.01); *A61B 17/3468* (2013.01); *A61B 2017/00407* (2013.01); *A61B 2017/00477* (2013.01); *A61B 2017/00867* (2013.01); *A61B 2017/00986* (2013.01); *A61B 2017/12054* (2013.01); *A61B 2090/037* (2016.02)

(58) Field of Classification Search
   CPC .............. A61B 17/128; A61B 17/1285; A61B 2017/00575; A61B 2017/00579; A61B 2017/00584; A61B 2017/00588; A61B 2017/00592; A61B 2017/00615; A61B 2017/00619; A61B 2017/00632; A61B 2017/0641; A61B 2017/0644; A61B 2017/12004; A61B 17/0643; A61B 2017/00606; A61F 6/204; A61F 6/206; A61F 6/208
   USPC ......................................... 606/158, 213, 215
   See application file for complete search history.

(56) References Cited

U.S. PATENT DOCUMENTS

| | | | |
|---|---|---|---|
| 4,235,238 A | 11/1980 | Ogiu | |
| 4,326,531 A | 4/1982 | Shimonaka | |
| 4,532,926 A | 8/1985 | O'Holla | |
| 4,548,202 A | 10/1985 | Duncan | |
| 4,573,469 A | 3/1986 | Golden | |
| 4,800,879 A | 1/1989 | Golyakhovsky | |
| 5,026,379 A | 6/1991 | Yoon | |
| 5,217,484 A | 6/1993 | Marks | |
| 5,282,811 A | 2/1994 | Booker | |
| 5,290,299 A | 3/1994 | Fain | |
| 5,334,217 A | 8/1994 | Das | |
| 5,536,275 A | 7/1996 | Bohrer | |
| 5,601,557 A | 2/1997 | Hayhurst | |
| 5,709,224 A | 1/1998 | Behl | |
| 5,865,791 A | 2/1999 | Whayne | |
| 5,947,994 A | 9/1999 | Louw | |
| 5,976,127 A | 11/1999 | Lax | |
| 6,071,292 A | 6/2000 | Makower | |
| 6,113,611 A | 9/2000 | Miller | |
| 6,132,438 A | 10/2000 | Fleischman | |
| 6,156,044 A | 12/2000 | Kammerer | |
| 6,312,446 B1 | 11/2001 | Huebsch | |
| 6,319,278 B1 | 11/2001 | Quinn | |
| 6,387,104 B1 | 5/2002 | Pugsley | |
| 6,458,153 B1 | 10/2002 | Bailey | |
| 6,485,504 B1 | 11/2002 | Johnson | |
| 6,491,707 B2 | 12/2002 | Makowerr | |
| 6,540,782 B1 | 4/2003 | Snyders | |
| 6,551,533 B1 | 4/2003 | Kuhn | |
| 6,565,581 B1 | 5/2003 | Spence | |
| 6,616,684 B1 | 9/2003 | Vidland | |
| 6,645,242 B1 | 11/2003 | Quinn | |
| 6,776,754 B1 | 8/2004 | Wilk | |
| 6,827,736 B2 | 12/2004 | Perouse | |
| 6,913,607 B2 | 7/2005 | Ainsworth | |
| 6,951,571 B1 | 10/2005 | Srivastava | |
| 6,960,220 B2 | 11/2005 | Marino | |
| 7,041,132 B2 | 5/2006 | Quijano | |
| 7,101,366 B2 | 9/2006 | Trout | |
| 7,149,587 B2 | 12/2006 | Wardle | |
| 7,220,274 B1 | 5/2007 | Quinn | |
| 7,416,554 B2 | 8/2008 | Lam | |
| 7,462,183 B2 | 12/2008 | Behl | |
| 7,766,816 B2 | 8/2010 | Chin | |
| 7,766,962 B1 | 8/2010 | Quinn | |
| 7,798,953 B1 | 9/2010 | Wilk | |
| 7,942,884 B2 | 5/2011 | Vahid | |
| 8,133,242 B1 | 3/2012 | Quinn | |
| 8,211,121 B1 | 7/2012 | Quinn | |
| 8,257,389 B2 | 9/2012 | Chanduszko | |
| 8,556,961 B2 | 10/2013 | Quinn | |
| 8,579,935 B2 | 11/2013 | DeVries | |
| 8,632,520 B2 | 1/2014 | Otley | |
| 8,870,946 B1 | 10/2014 | Quinn | |
| 9,173,712 B2 | 11/2015 | Annest | |
| 2003/0004568 A1 | 1/2003 | Ken | |
| 2003/0105473 A1 | 6/2003 | Miller | |
| 2003/0120286 A1 | 6/2003 | Burbank | |
| 2003/0139819 A1 | 7/2003 | De Beer | |
| 2003/0171771 A1 | 9/2003 | Anderson | |
| 2003/0199963 A1 | 10/2003 | Tower | |
| 2003/0199972 A1 | 10/2003 | Zadno-Azizi | |
| 2004/0044364 A1 | 3/2004 | DeVries | |
| 2004/0138684 A1 | 7/2004 | Elon | |
| 2004/0215339 A1 | 10/2004 | Drasler | |
| 2005/0004652 A1 | 1/2005 | Van Der Burg | |
| 2005/0038460 A1 | 2/2005 | Jayaraman | |
| 2005/0137682 A1 | 6/2005 | Justino | |
| 2005/0267524 A1 | 12/2005 | Chanduszko | |
| 2005/0267529 A1 | 12/2005 | Crockett | |
| 2005/0277966 A1 | 12/2005 | Ewers | |
| 2005/0288786 A1 | 12/2005 | Chanduszko | |
| 2006/0264987 A1 | 11/2006 | Sgro | |
| 2006/0271103 A1 | 11/2006 | Ferrari | |
| 2007/0027466 A1 | 2/2007 | Ortiz | |
| 2007/0043349 A1 | 2/2007 | Swanson | |
| 2007/0073337 A1 | 3/2007 | Abbott | |
| 2007/0106328 A1 | 5/2007 | Wardle | |
| 2007/0135826 A1 | 6/2007 | Zaver | |
| 2007/0144539 A1 | 6/2007 | Van der Burg | |
| 2007/0179527 A1 | 8/2007 | Eskuri | |
| 2007/0265658 A1 | 11/2007 | Nelson | |
| 2008/0004640 A1 | 1/2008 | Ellingwood | |
| 2008/0077180 A1 | 3/2008 | Kladakis | |
| 2008/0109066 A1 | 5/2008 | Quinn | |
| 2008/0208226 A1 | 8/2008 | Seibold | |
| 2008/0306495 A1 | 12/2008 | Thompson | |
| 2009/0084386 A1* | 4/2009 | McClellan | A61F 6/225 128/831 |
| 2009/0114233 A1 | 5/2009 | Edoga | |
| 2009/0157174 A1 | 6/2009 | Yoganathan | |
| 2010/0004740 A1 | 1/2010 | Seguin | |

(56) References Cited

U.S. PATENT DOCUMENTS

| | | |
|---|---|---|
| 2010/0198254 A1 | 8/2010 | Schaeffer |
| 2010/0228269 A1 | 9/2010 | Gamson |
| 2010/0234880 A1 | 9/2010 | Abbott |
| 2011/0082495 A1 | 4/2011 | Ruiz |
| 2011/0108039 A1 | 5/2011 | Frigstad |
| 2011/0152902 A1 | 6/2011 | Kurrus |
| 2011/0295302 A1 | 12/2011 | Mohl |
| 2011/0319906 A1 | 12/2011 | Rudakov |
| 2012/0232569 A1 | 9/2012 | Wright |
| 2012/0283758 A1 | 11/2012 | Miller |
| 2013/0046331 A1 | 2/2013 | Christensen |
| 2013/0218259 A1 | 8/2013 | Quinn |
| 2013/0274857 A1 | 10/2013 | Quinn |
| 2014/0100460 A1 | 4/2014 | Otley |
| 2015/0094740 A1 | 4/2015 | Gagne |
| 2015/0201947 A1 | 7/2015 | Hill |

FOREIGN PATENT DOCUMENTS

| | | |
|---|---|---|
| EP | 2311381 | 4/2011 |
| WO | WO 2005/006990 | 1/2005 |
| WO | WO 2006/130836 | 7/2006 |
| WO | WO 2007/006286 | 1/2007 |
| WO | WO 2008/115922 | 9/2008 |
| WO | WO 2009/029914 | 3/2009 |
| WO | WO 2010/127083 | 11/2010 |

\* cited by examiner

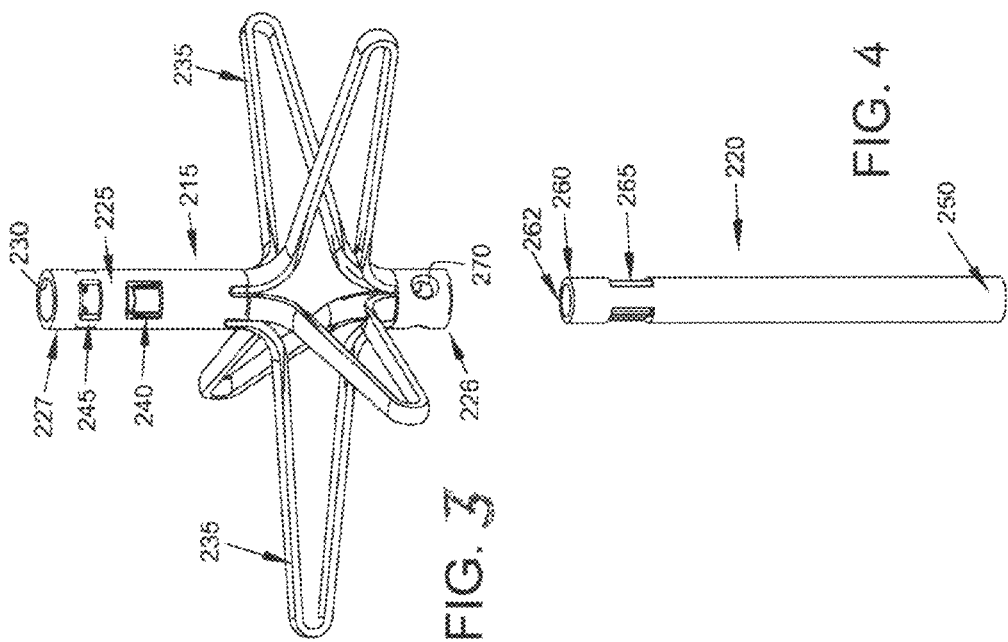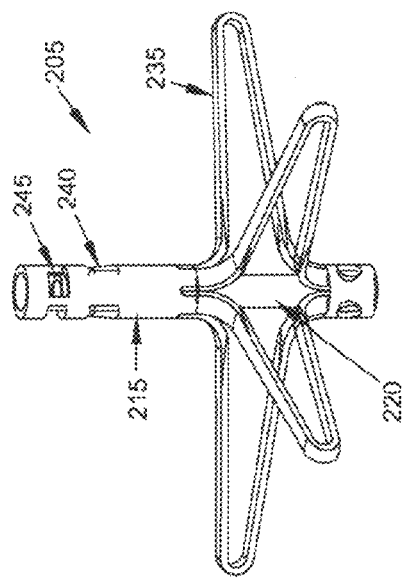

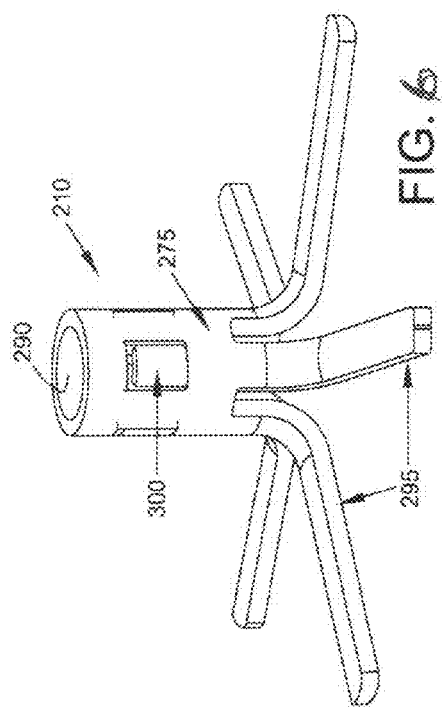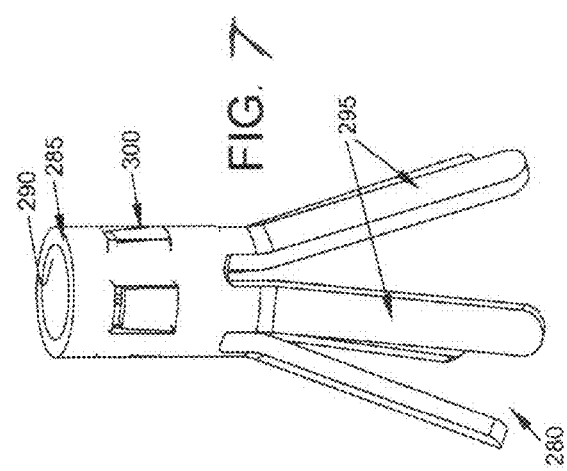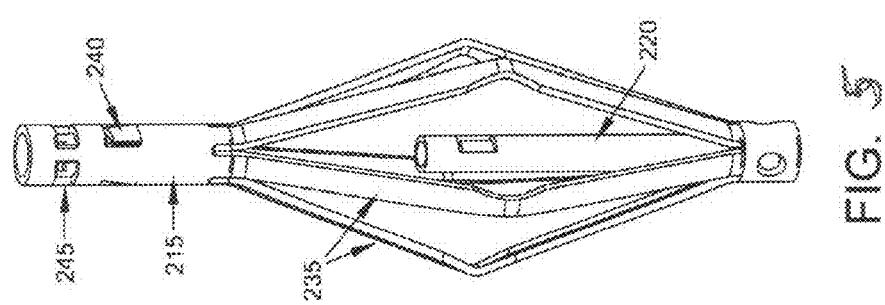

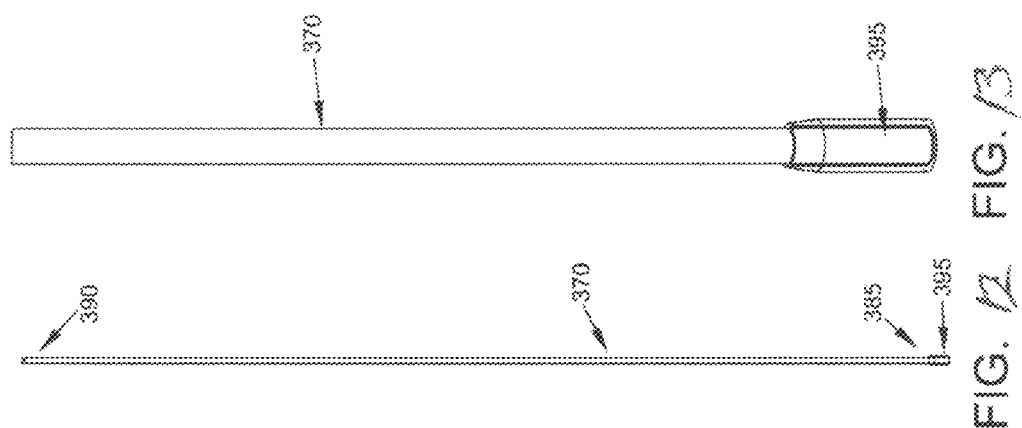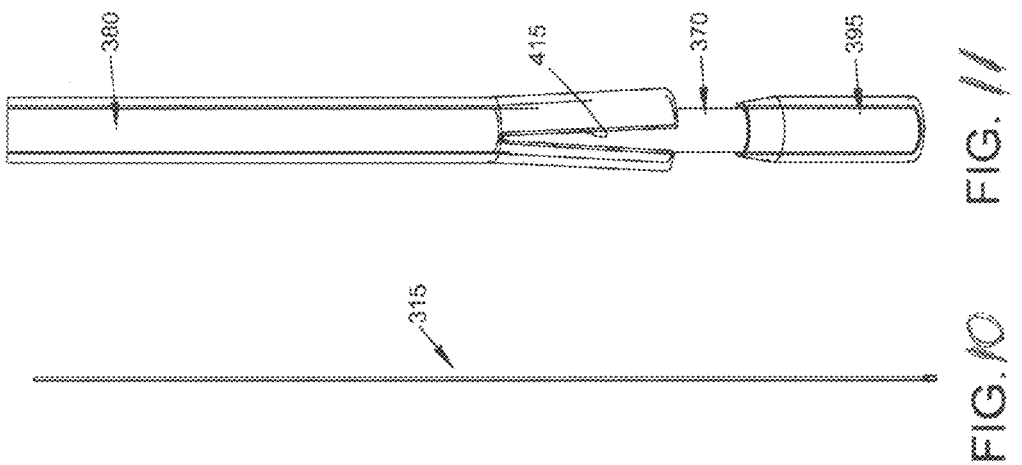

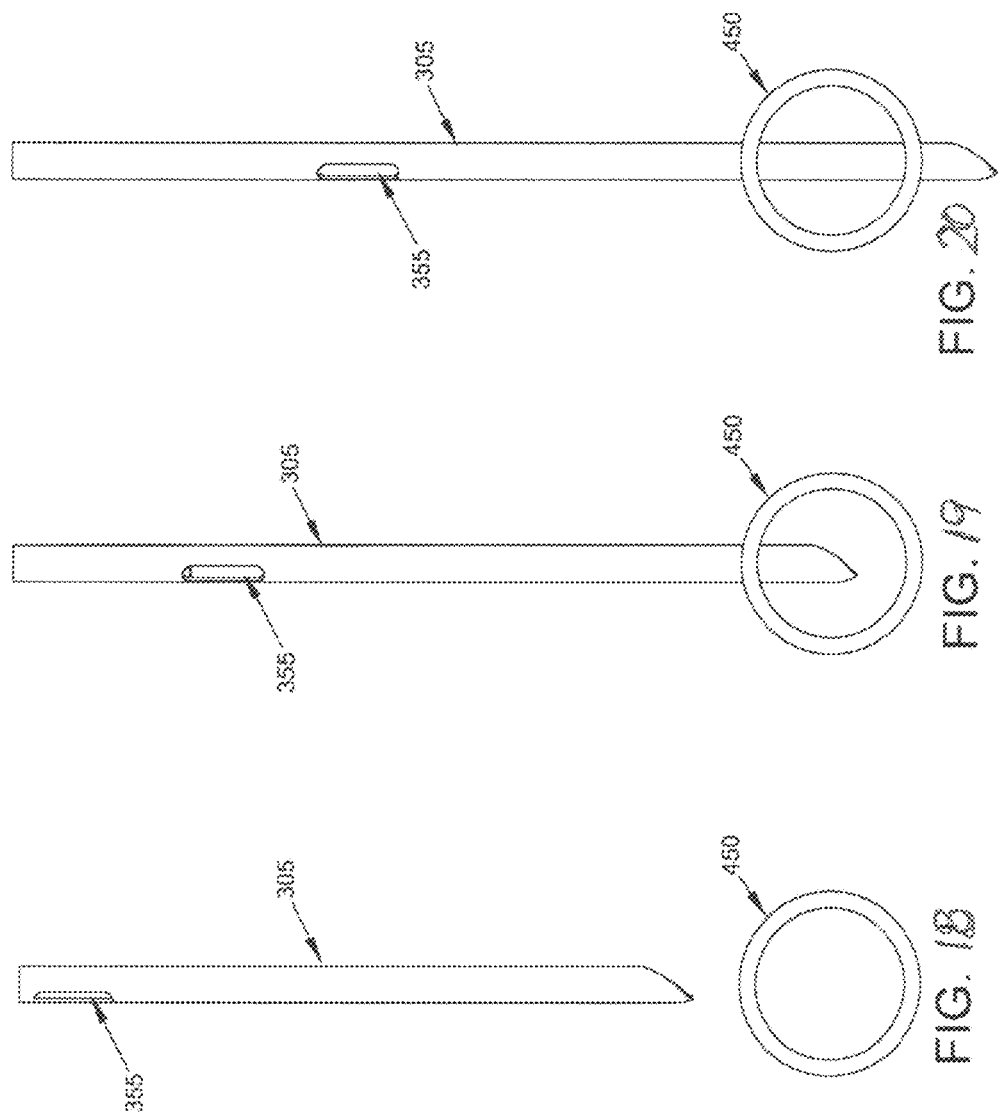

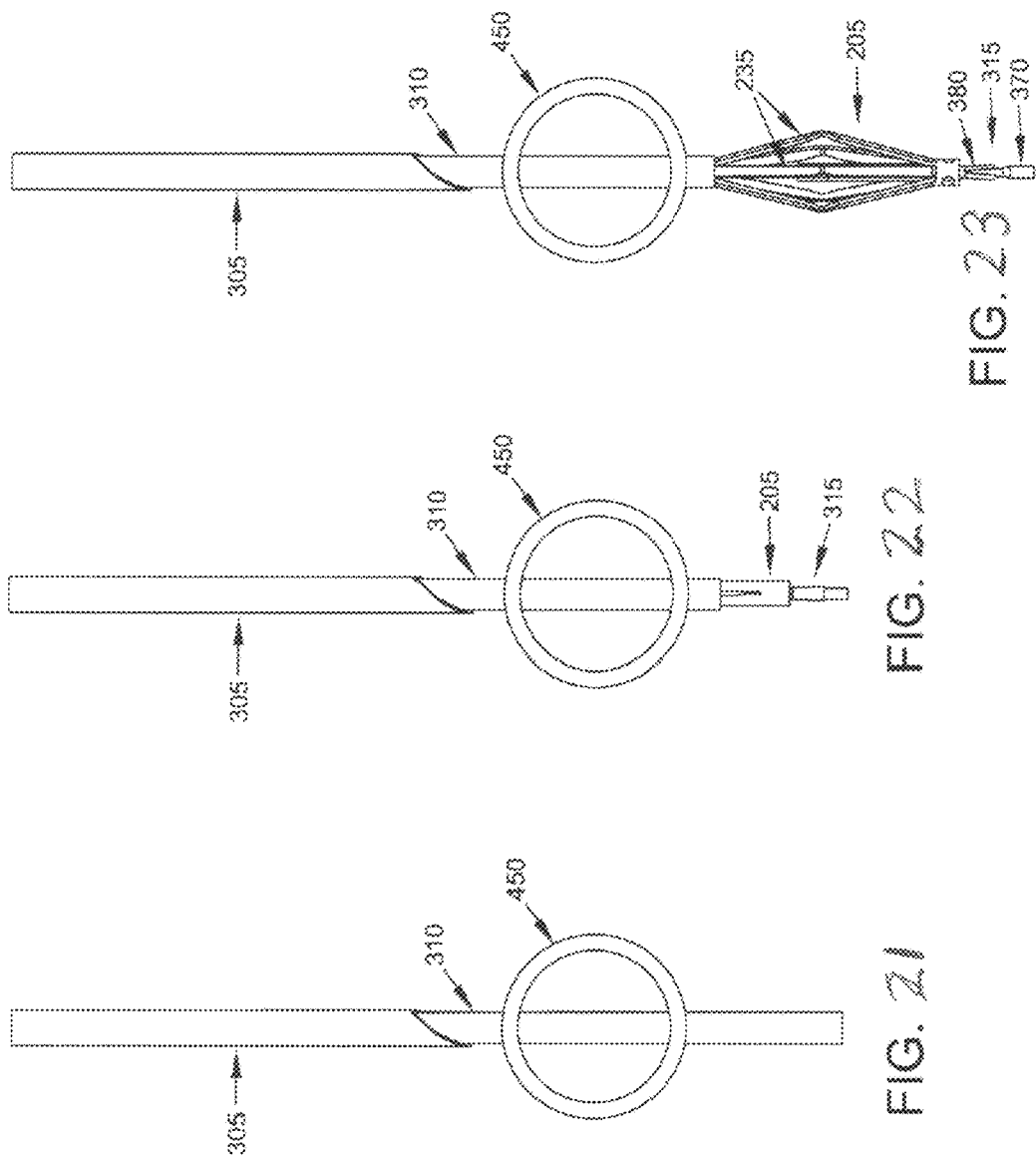

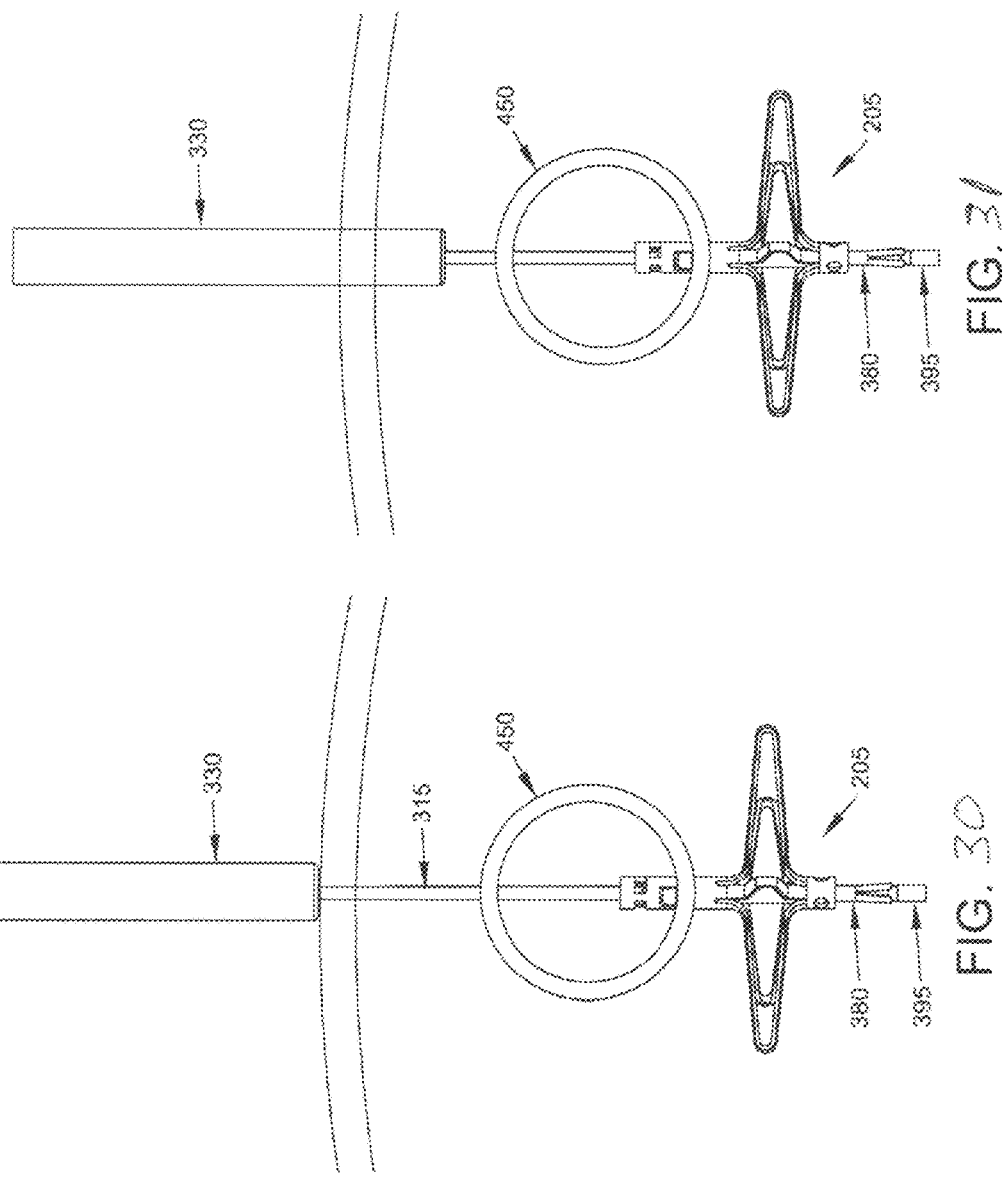

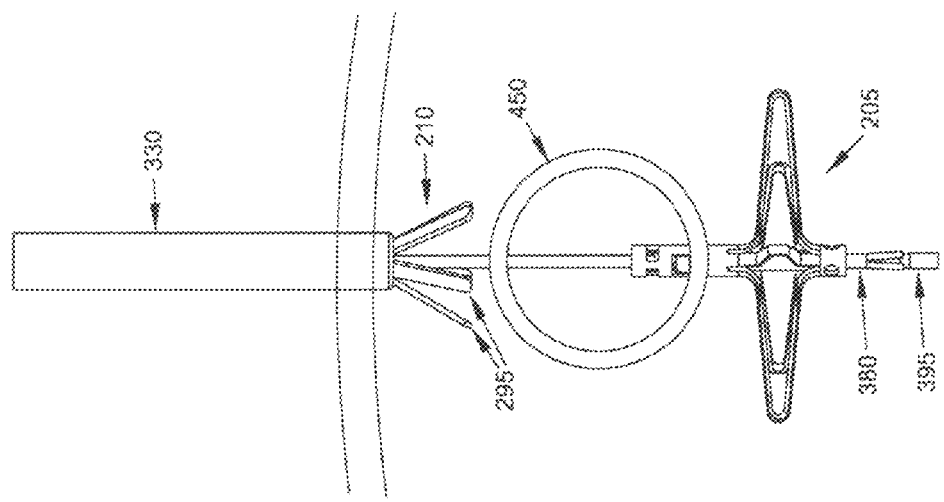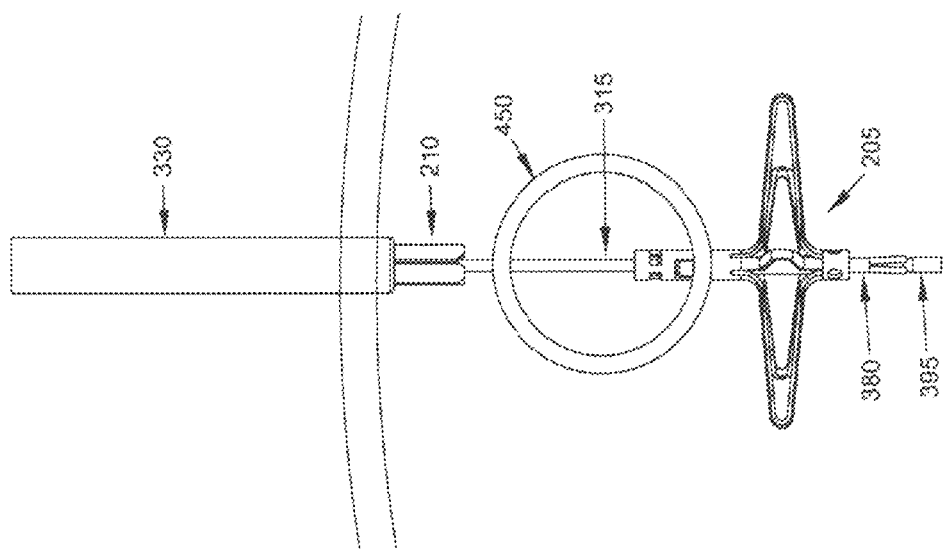

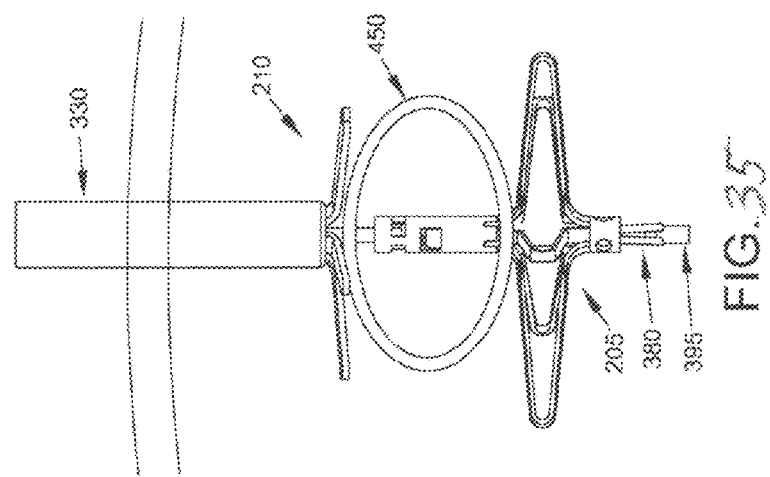
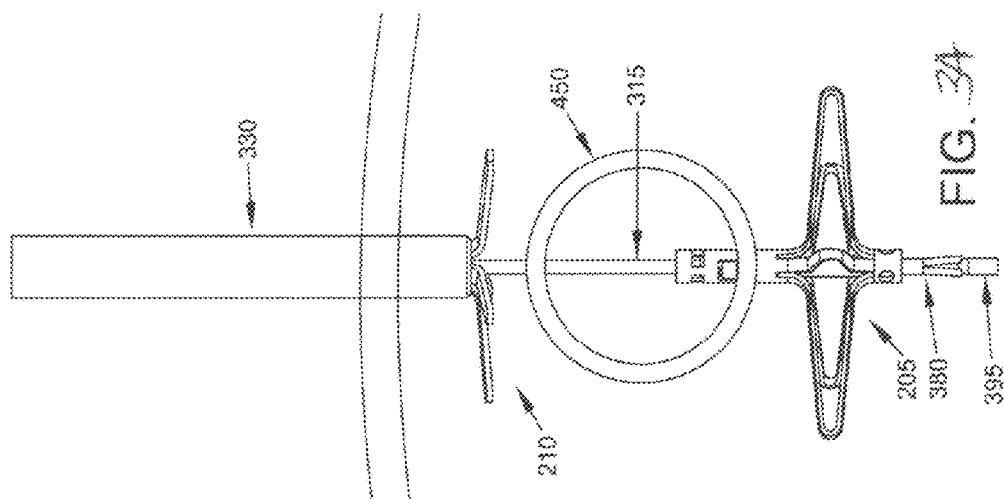

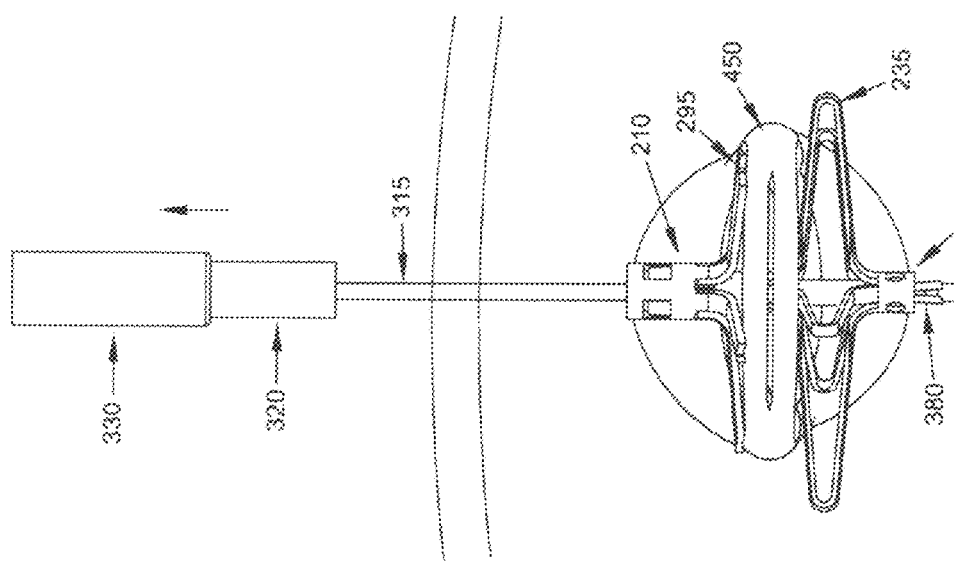
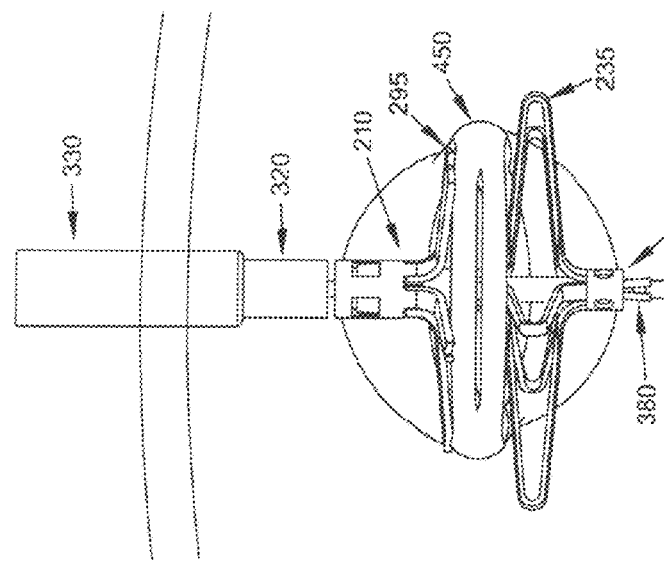

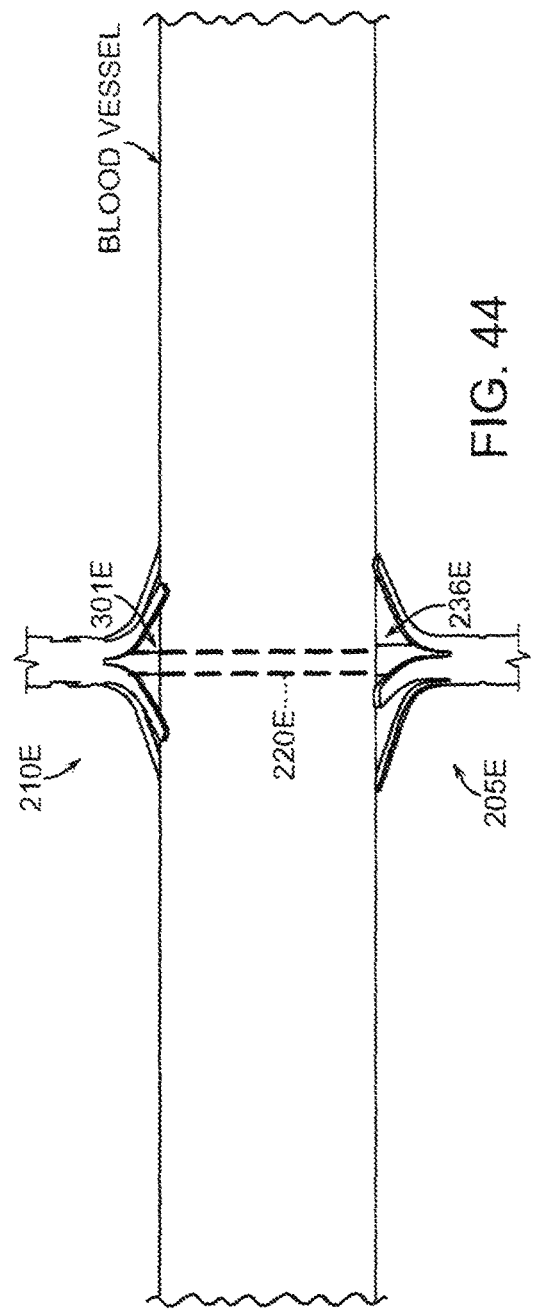
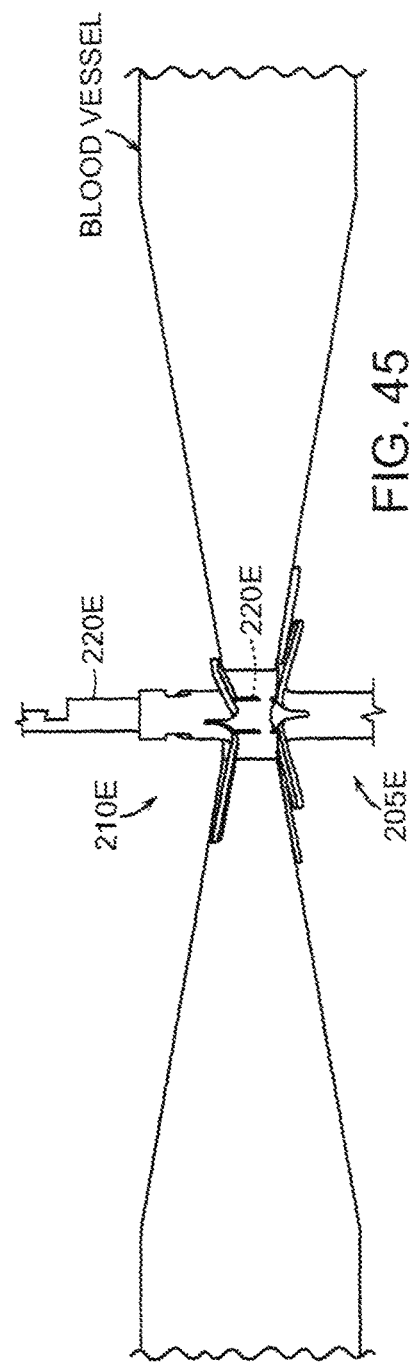

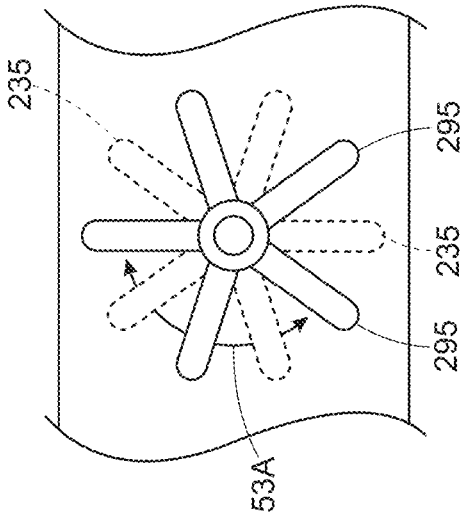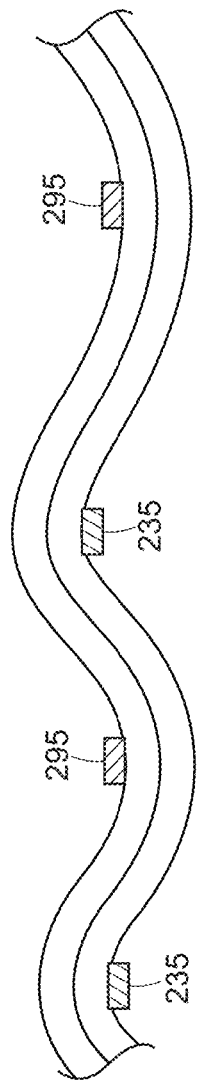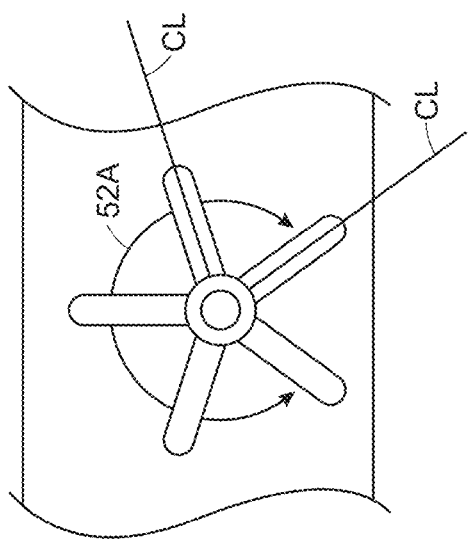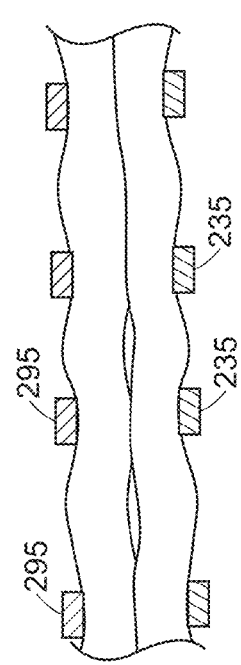

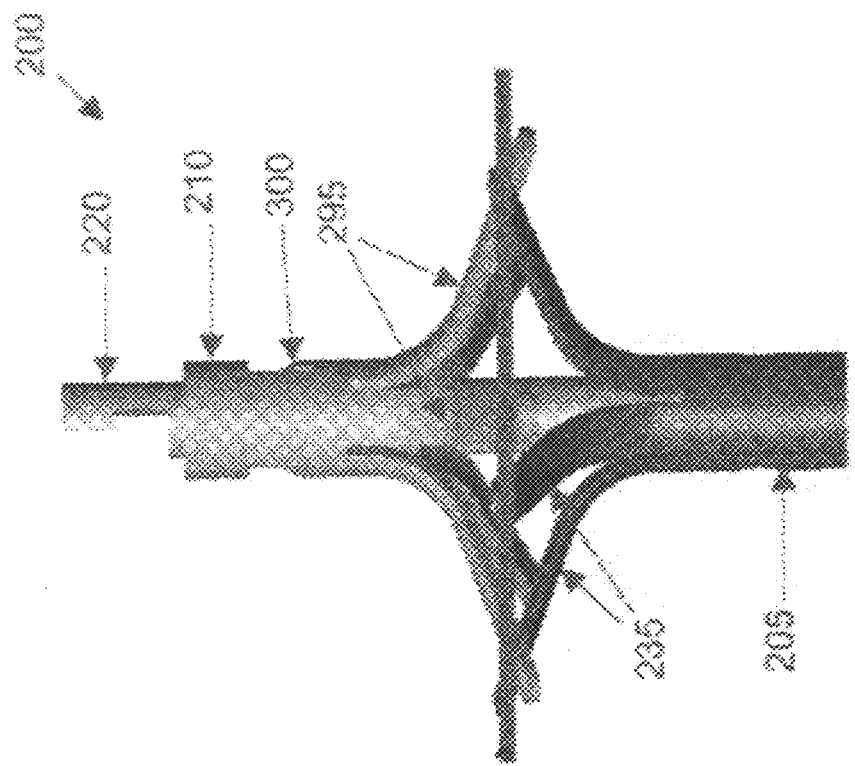

METHOD AND APPARATUS FOR CLAMPING TISSUE LAYERS AND OCCLUDING TUBULAR BODY STRUCTURES

REFERENCE TO PENDING PRIOR PATENT APPLICATIONS

This is a continuation-in-part patent application (35 USC § 120) of pending U.S. patent application Ser. No. 14/639,814, filed Mar. 5, 2015 which
(i) is a continuation-in-part of pending prior U.S. patent application Ser. No. 14/272,304, filed May 7, 2014, which
   (1) is a continuation-in-part of prior U.S. patent application Ser. No. 13/857,424, filed Apr. 5, 2013, which is
      (a) is a continuation-in-part of prior U.S. patent application Ser. No. 13/348,416, filed Jan. 11, 2012, which patent application claims benefit of prior U.S. Provisional Patent Application Ser. No. 61/431,609, filed Jan. 11, 2011 and
      (b) claims benefit of prior U.S. Provisional Patent Application Ser. No. 61/620,787, filed Apr. 5, 2012
   (2) and claims benefit of prior U.S. Provisional Patent Application Ser. No. 61/820,589, filed May 7, 2013 and
(ii) claims benefit of prior U.S. Provisional Patent Application Ser. No. 61/948,241, filed Mar. 5, 2014 by; and
(iii) claims benefit of prior U.S. Provisional Patent Application Ser. No. 62/084,989, filed Nov. 26, 2014.

The disclosures of the nine (9) above-identified patent applications are hereby incorporated by reference in their entireties as if fully set forth herein. Applicants claim priority to each of them.

FIELD OF INVENTION

The invention relates to methods and devices for the occlusion of blood vessels and other tubular body structures and for clamping tissue layers together.

BACKGROUND

There are numerous medical conditions and procedures in which it is desirable or necessary to occlude hollow or tubular body organs such as, for example, blood vessels or to clamp together layers of tissue. One such example is in the treatment of venous complications, such as varicose veins, in which treatment involves selective occlusion of the veins. Other ducts, vessels or hollow body organs also may have to be obstructed or tissue layers clamped together for a variety of reasons. It would be desirable to provide devices and methods to effect occlusions of hollow body organs and to secure tissue layers to each other in a manner that that is easy and quick to apply.

SUMMARY

The present invention provides a new and improved minimally invasive approach for occluding tubular body structures such as, for example, for treating varicose veins and other blood vessels where occlusion of the vessel or organ is an appropriate remedy.

More particularly, the inventions comprise the provision and use of an occluder that is used to occlude a vessel so as to restrict blood flow through the vessel. It may be used, for example, to treat varicose veins below the point of occlusion. Significantly, the device is configured to be deployed using visualization as may be provided by ultrasound and/or other visualization apparatus (e.g., CT, MRI, X-ray etc.). As a result, the treatment may be provided in a doctor's office with minimal local anesthetic and effectively no post-operative care. The invention also may be utilized in other procedures under direct visualization (e.g., during "open" surgery) or under indirect visualization such as during laparoscopic surgery where visualization is provided through the use of a scope, or during percutaneous surgery where visualization is provided through the use of imaging apparatus such as an ultrasound imager, an X-ray imager, etc.

In one form of the invention, there is provided apparatus for occluding a blood vessel, the apparatus comprising: an occluder having two cooperative parts, each of which includes a plurality of legs configured to assume (i) a diametrically reduced configuration for disposition within the lumen of a tube, and (ii) a diametrically expanded configuration in which the legs are extended radially for disposition adjacent to the blood vessel, such that when the two parts of the expanded occluder are brought together in their diametrically-expanded configuration with the vessel between them so they can grip the vessel to occlude it. In one aspect of this form of the invention the legs of the two parts are in registry when they grip the vessel. In another aspect of this form of the invention, the legs of the two parts of the occluder are interdigitated when they grip the vessel.

In another aspect of the invention, a method for occluding a blood vessel is provided in which opposing walls of the vessel are clamped directly together and in which the clamping is effected directly along a plurality of radially extending lines that extend outwardly from the axis of the occluder. In another aspect of the invention the opposing walls are bought together by constraining them in a serpentine pattern characterized by a series of reversing bends that extend circumferentially about the occluder axis. In a further aspect of the invention a clamping or occlusion device is provided in which the tissue is transfixed but in which leakage of fluids (e.g., blood) from the transfixion puncture is minimized.

DESCRIPTION OF THE DRAWINGS

The various objects and advantages of the invention will be appreciated from the following description with reference to the accompanying drawings in which:

FIG. 2 is an isometric illustration of the distal implant with its legs expanded;

FIG. 3 is an isometric illustration of the distal implant with the locking tube removed;

FIG. 4 is an illustration of the locking tube;

FIG. 5 is an illustration of the distal implant partially collapsed;

FIG. 6 is an isometric illustration of the proximal implant with the legs of the implants being in their relaxed, expanded configuration;

FIG. 10 illustrates a composite guidewire usable in deployment of the occluder;

FIG. 11 illustrates, in larger detail, the distal end of the composite guidewire;

FIG. 12 illustrates a guidewire rod component of the composite guidewire;

FIG. 13 illustrates, in enlarged detail, the distal end of the guidewire rod;

FIGS. 18-41 are sequential, diagrammatic illustrations of the manner in which the two-piece occluder is delivered and deployed to occlude a tubular vessel;

FIGS. 44 and 45 are diagrammatic illustrations of an occluder before and after it has occluded a vessel;

FIG. 52 is a diagrammatic, plan view of an occluder as seen from the proximal side in which the legs of the proximal implant and distal implant are in registry with each other so as to clamp directly tissue engaged between the proximal and distal implants;

FIG. 52A is a sectional illustration as seen along the circumferential line 52A of FIG. 52 showing the manner in which the legs 235, 295 of the implants are in registry and compress directly the opposing walls of an occluded vessel;

FIG. 53 is an illustration similar to that of FIG. 52 but in which the legs of the proximal and distal implants are interdigitated;

FIG. 53A is a sectional illustration as seen along the circumferential line 53A of FIG. 53 showing the manner in which the interdigitated legs 235, 295 of the implants are oriented and the manner in which the interdigitated legs constrain the tissue layers in a series of sequential, alternating and reversing serpentine bends;

FIG. 54 is a diagrammatic side elevation of the occluder in which the legs of the implants are interdigitated and where the ends of the legs are overlapped;

FIGS. 69-72 are enlarged cross sectional illustrations of engaged proximal and distal implants with multiple windows and tangs showing the manner in which they engage each other;

ILLUSTRATIVE EMBODIMENTS

Figure 1:
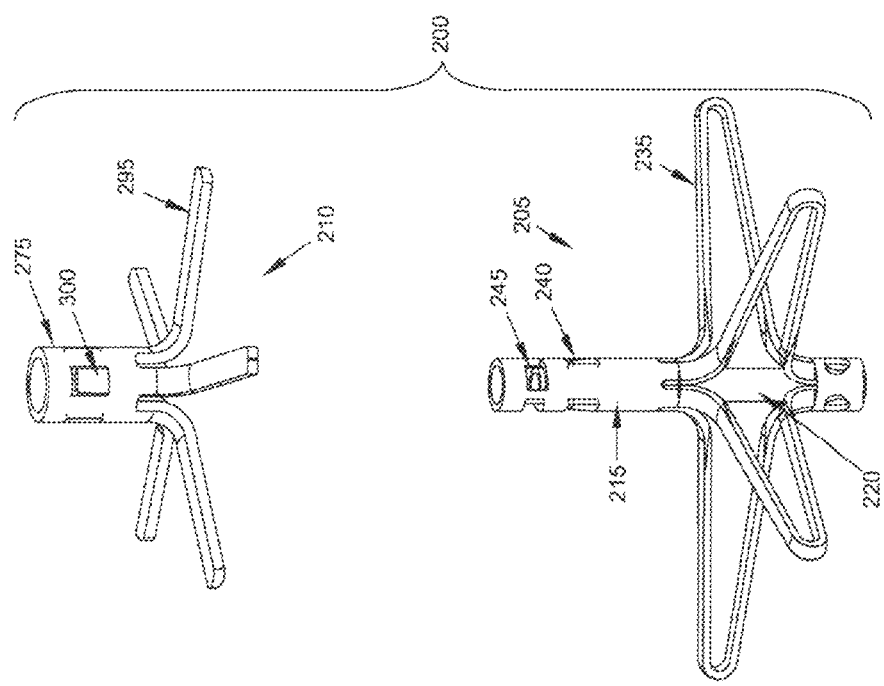
FIG. 1 is an isometric illustration of the proximal and distal implants of a two-part occluder of the invention with the legs of the implants being in their relaxed, expanded configuration.
Figure 43:
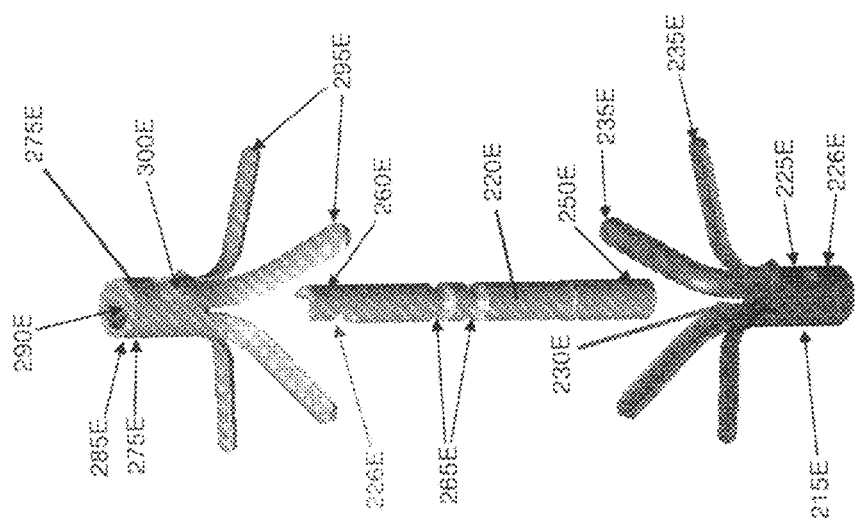
FIG. 43 is an exploded illustration of the embodiment of FIG. 42.

FIG. 1 shows an embodiment of a two-part occluder 200 formed in accordance with the present invention. Two-part occluder 200 generally comprises a distal implant 205 and a proximal implant 210. The occluder functions by compressing and securing the opposed walls of the vessel together. In one embodiment, distal implant 205, shown in further detail in FIGS. 2-6, comprises a body 215 comprising a tube 225 having a distal end 226, a proximal end 227, and a lumen 230. A locking tube 220 is located within lumen 230 of the body 215. The tubular body 215 is slit intermediate its length so as to define a plurality of segments that, when the body is axially collapsed, will deform to define a plurality of radially extending legs 235. Distal implant body 215 preferably is formed out of an elastic material (e.g., a shape memory material having superelastic properties such as Nitinol or superelastic polymers, including superelastic plastics) and constructed so that the legs 235 normally are bent and project laterally away from the longitudinal axis of tube 225 (e.g., in the manner shown in FIGS. 2 and 3). Due to the elastic nature of the material used to form distal implant body 215, legs 235 can be deformed to a tubular, substantially linear, low profile shape so that they can be constrained within the lumen of a delivery tube or needle. See, for example, FIG. 5, which shows legs 235 moved inwardly toward a low profile relative to the position shown in FIGS. 2 and 3. However, when the constraint is removed, the elasticity of the material of the body 215 causes legs 235 to return to their relaxed, expanded position shown in FIGS. 43 and 44.

The lower, distal end 250 of the locking tube 220 is secured to the lower end of the body 215 as by spot welds applied via openings 270 formed in the distal end 226 of distal body 215 so that distal body and locking tube form a singular structure (see FIGS. 3 and 5). This enables the proximal end 227 of the tubular body 215 to move longitudinally in a distal direction along the locking tube. When distal implant 205 is in its substantially linear, low profile condition (i.e., with legs 235 restrained in an in-line condition), distal implant locking tube 220 terminates well short of tangs 240 formed in the distal implant body 215, so that the proximal end 227 of distal implant body 215 can move longitudinally relative to distal end 226 of distal implant body 215.

The distal implant includes an arrangement by which it can be locked in the radially expanded configuration shown in FIG. 2. To that end, inwardly projecting tangs 240 are formed in tube 225 near the proximal end 227. Tang-receptive windows 265 are formed in the proximal region of the locking tube 220. The tangs and windows are positioned so that when the proximal end 227 of body 215 is moved distally a sufficient distance to allow full radial expansion of legs 235 (see FIG. 1), locking tangs 240 of distal implant body 215 will be received within windows 265 of the locking tube 220 to lock distal implant 205 in its radially-expanded condition (FIGS. 2 and 3).

Figure 7D:
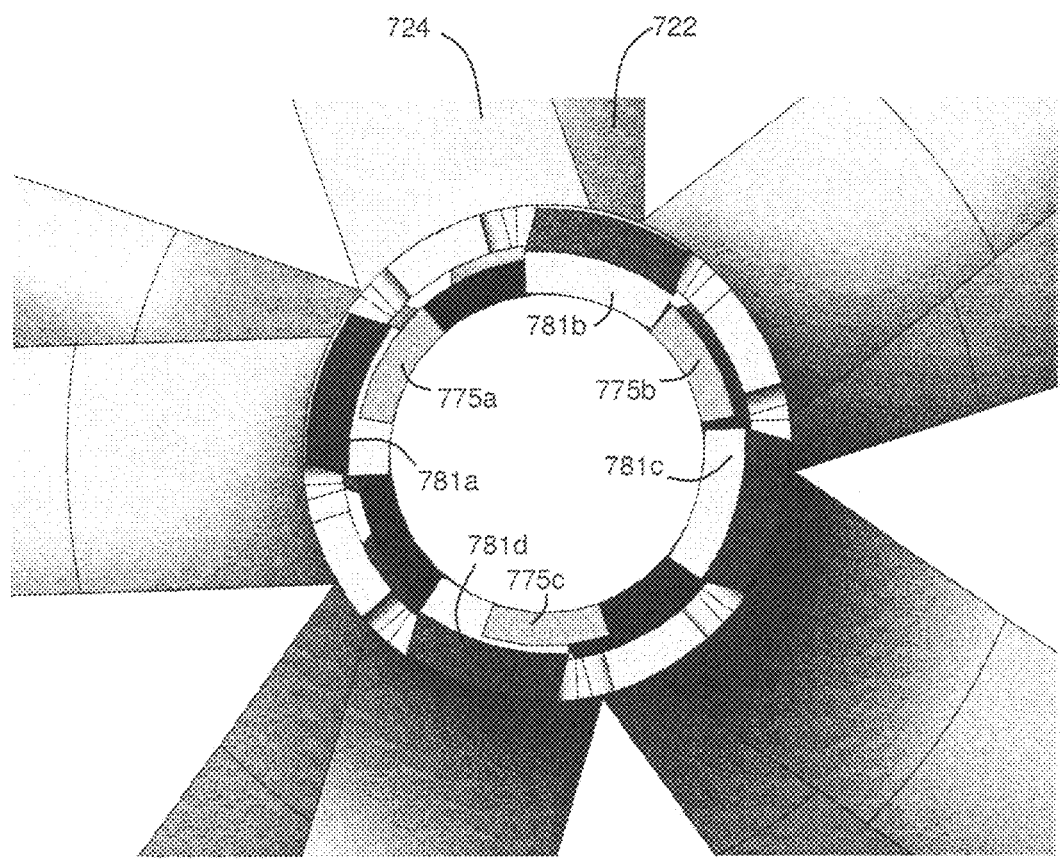
FIG. 7 is an illustration of the proximal implant with its legs partially collapsed.
Figure 7I:
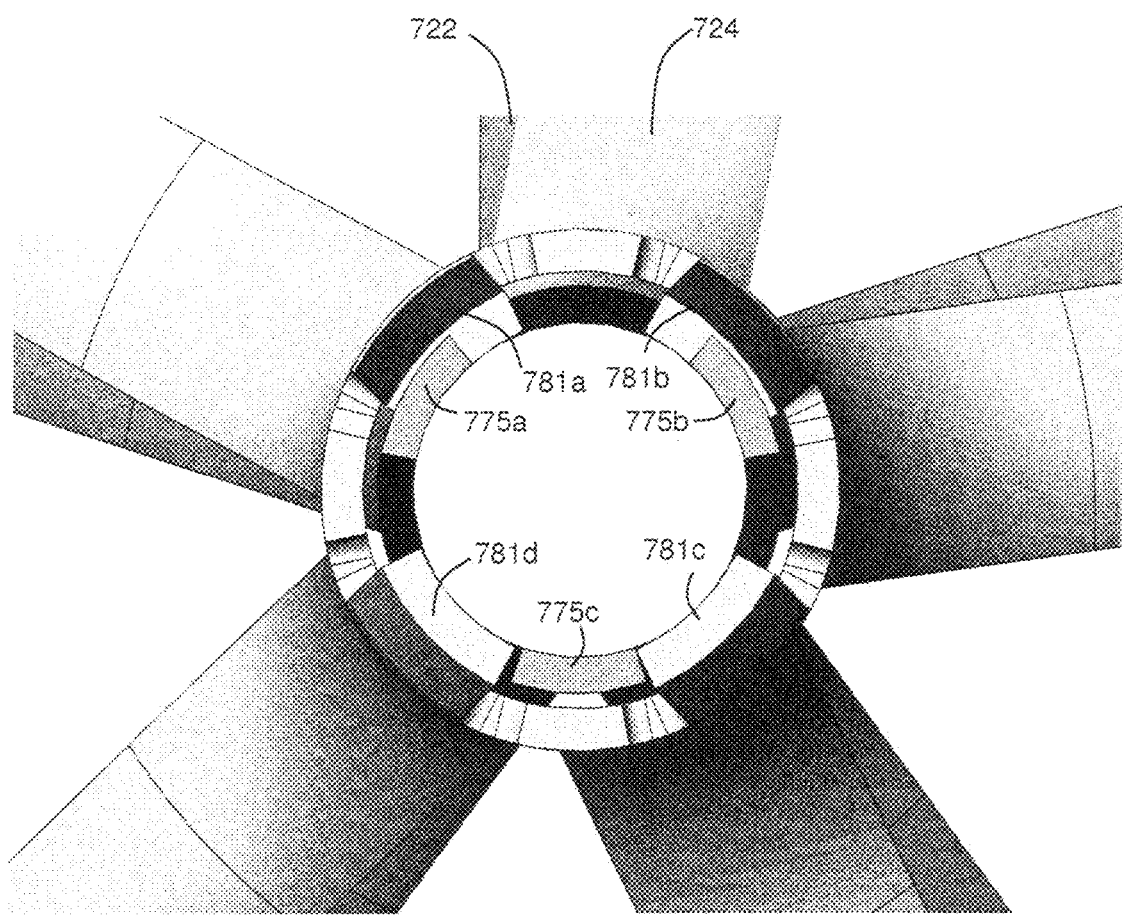
Figure 7Z:
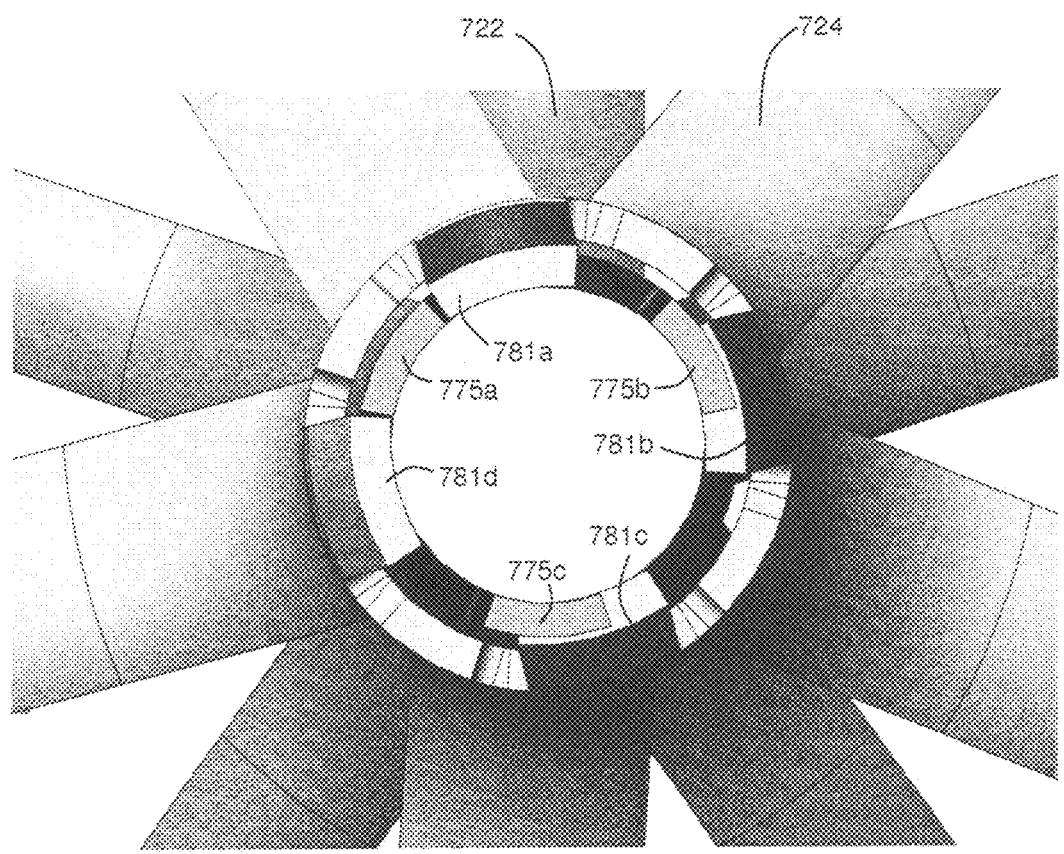

FIGS. 6 and 7 illustrate the proximal implant 210 that comprises a tube 275 having a distal end 280, a proximal end 285, and a lumen 290 adapted to receive the proximal end 227 of the tubular body 215 of the distal implant 205. Tube 275 is slit at its distal end to define a plurality of legs 295. One or more inwardly projecting tangs 300 are formed in tube 275 adjacent its proximal end 285. Proximal implant 210 is preferably formed out of the same or similar material as the distal implant and is constructed so that its legs 295 normally project laterally away from the longitudinal axis of tube 275 (e.g., in the manner shown in FIG. 6). Legs 295 can be constrained inwardly to a low profile configuration so that proximal implant 210 can assume a substantially linear disposition to be contained within the lumen of a delivery tube. See, for example, FIG. 7, which shows legs 295 moved inwardly relative to the position shown in FIG. 6. However, when the constraint is removed, the elastic nature of the material causes legs 295 to return to the expanded position shown in FIG. 6.

The distal and proximal implants 205, 210 can be mated (with tube 225 of distal implant body 215 being received in lumen 290 of proximal implant 210) so that the expanded legs 235 of distal implant 205 oppose and are in registry with the expanded legs 295 of proximal implant 210 (see, for example, FIGS. 52 and 52A). That arrangement imposes a direct clamping action on a blood vessel (e.g., vein) or other tissue disposed between the registered legs to occlude the blood vessel. In that mode of clamping the walls of the vessel are pressed together along a series of circumferentially spaced, radially extending lines. In another aspect of the invention, the proximal and distal implants may be arranged so that the legs of one are interdigitated with the legs of the other which imposes a different, serpentine, clamping configuration. Interdigitation refers to an arrangement that, when the proximal and distal implants are connected the legs 295 of the proximal implant will overlie the spaces between the legs 235 of the distal implant (or vice versa), as discussed in further detail below. The distal implant 205 and proximal implant 210 are configured to lock together in a clamped position by cooperative engagement of tangs 300 of proximal implant 210 and tang-receptive windows 245 of distal implant 205.

Figure 9:
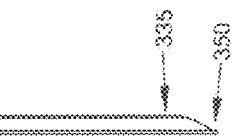
FIG. 9 illustrates a distal implant delivery tube.
Figure 8:
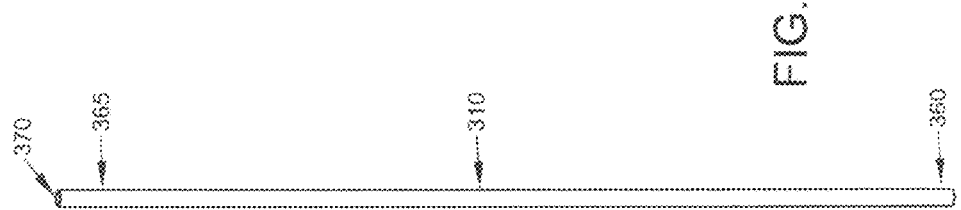
FIG. 8 illustrates a delivery needle that may be used to deliver and deploy the occluder.
Figure 17:
FIG. 17 illustrates the proximal implant delivery tube.
Figure 16:
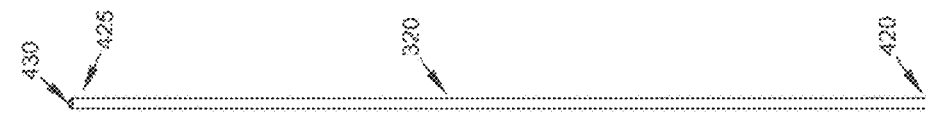
FIG. 16 illustrates the pushrod of the delivery system.
Figure 15:
FIG. 15 illustrates, in enlarged detail, the distal end of the guidewire sheath.
Figure 14:
FIG. 14 illustrates the guidewire sheath component of the composite guidewire.

Two-part occluder 200 may be deployed using associated installation apparatus that comprises a hollow needle 305 (FIG. 8) for penetrating tissue, a distal implant delivery tube 310 (FIG. 9) that extends through the needle, for delivering distal implant 205 through hollow needle 305 to the far side of the blood vessel which is to be occluded, a composite guidewire 315 (FIGS. 10-15) having a selectively expandable distal tip for providing support to various components during delivery and deployment, and a proximal implant delivery tube 330 (FIG. 17) for delivering proximal implant 210 and for mating with distal implant 205, as discussed below. The installation apparatus also may include a separate tubular push rod 320 (FIG. 16) that is used in deployment of both the distal and proximal implants.

Hollow needle 305 (FIG. 8) has a distal end 335, a proximal end 340 and a lumen 345. Distal end 335 terminates in a sharp point 350. Hollow needle 305 may comprise a side port 355 that communicates with lumen 345. Distal implant delivery tube 310 (FIG. 9) has a distal end 360, a proximal end 365 and a lumen 370. Composite guidewire 315 (FIGS. 10-15) comprises a guidewire rod 370 and a guidewire sheath 380. Guidewire rod 370 has a distal end 385 and a proximal end 390. Distal end 385 terminates in an enlargement 395. Guidewire sheath 380 comprises a distal end 400, a proximal end 405 and a lumen 410 that receives the guidewire rod 370. The distal end 400 of guidewire sheath 380 has at least one, and preferably a plurality of, proximally extending slits 415 that are open on the distal end of guidewire sheath 380 and allow the distal end of guidewire sheath 380 to expand radially when guidewire rod 370 is urged proximally within the sheath 380. Tubular push rod 320 (FIG. 16) has a distal end 420, a proximal end 425 and a lumen 430. Proximal implant delivery tube 330 (FIG. 17) has a distal end 435, a proximal end 440 and a lumen 445.

Figure 24:
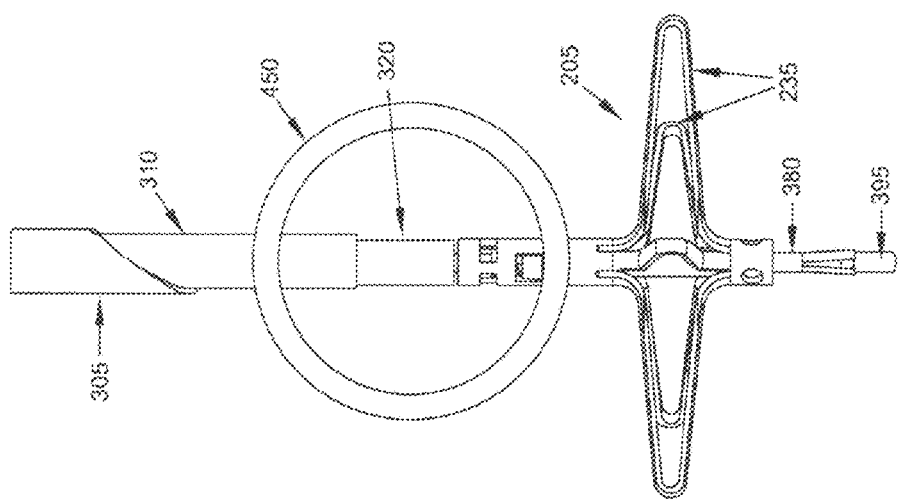
Figure 25:
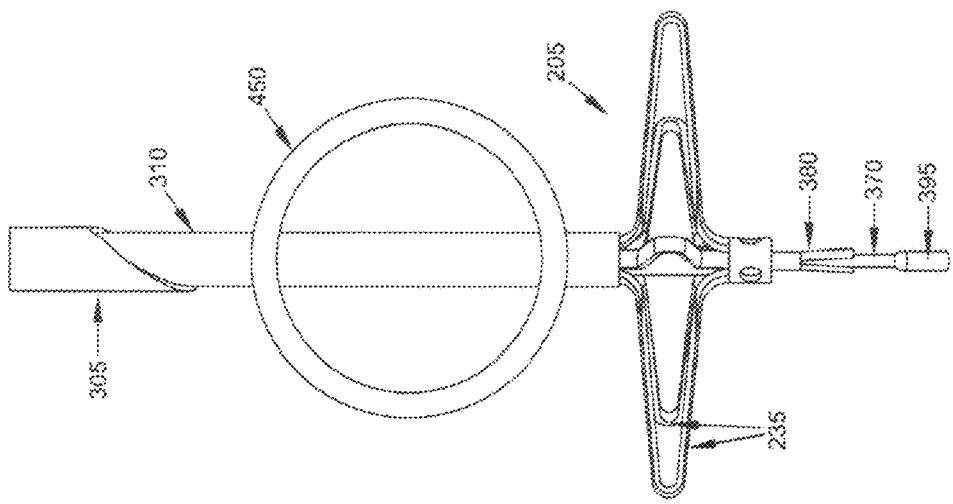
Figure 27:
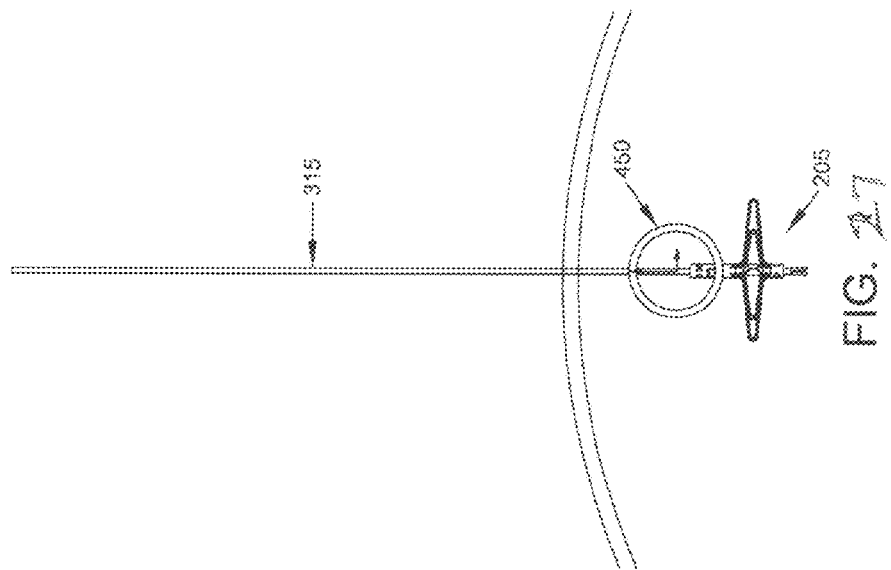
Figure 26:
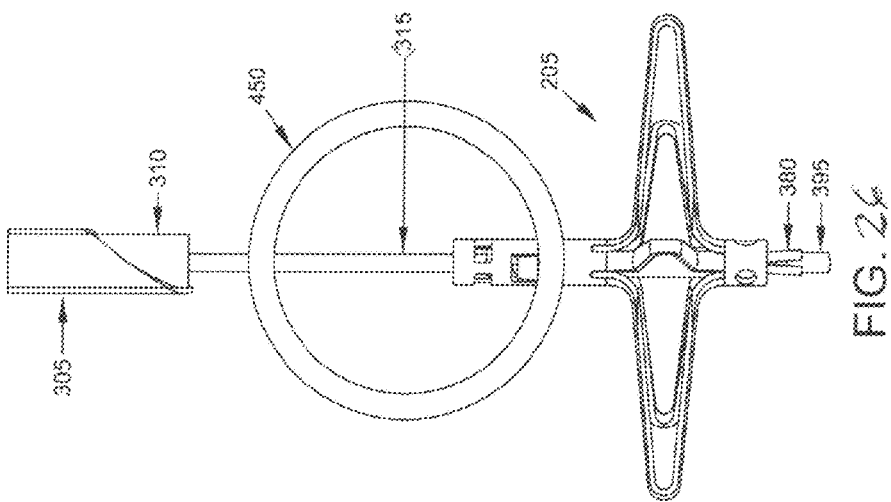
Figure 29:
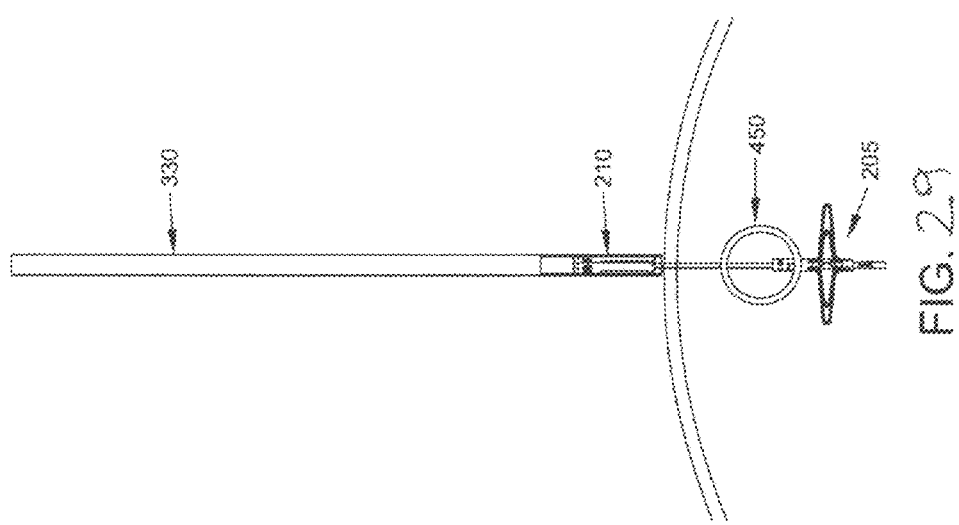
Figure 28:
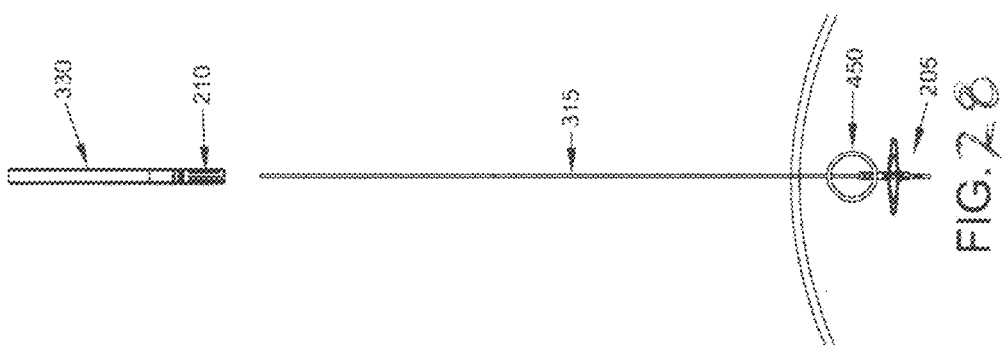

Two-part occluder 200 and its associated installation apparatus are used as follows. First, hollow needle 305 carrying distal implant delivery tube 310 therein, which in turn contains the composite guidewire 315 upon which is mounted distal implant 205 is passed through the skin of the patient, through intervening tissue, and across the blood vessel (e.g., vein 450) that is to be occluded (FIGS. 18-20). As this is done, any blood flowing out side port 355 can be monitored—excessive or pulsatile blood flow can indicate that hollow needle has accidentally struck an artery. Next, hollow needle 305 is retracted, leaving distal implant delivery tube 310 extending across the blood vessel (FIG. 21). The distal implant delivery tube 310 then is retracted partially to expose the distal ends of composite guidewire and distal implant 205 (FIG. 22). Next, push rod 320 is advanced over composite guidewire 315 to advance the distal implant 205 and composite guidewire 315 out of the distal end of distal implant delivery tube 310. As this occurs, legs 235 of distal implant 205 are released from the constraint of distal implant delivery tube 310 and its legs expand radially as shown in FIGS. 23 and 24. Then, with push rod 320 being held in place against the proximal end of distal implant 205, composite guidewire 315 is expanded at its distal end and is pulled proximally so as to bring the distal and proximal implants together until locking tangs 240 of distal implant body 215 engage windows 265 of the locking tube 220, thus securing the expanded implants together (FIG. 25). At this point, hollow needle 305, distal implant delivery tube 310 and push rod 320 may be removed (FIG. 26), leaving distal implant 205 mounted on composite guidewire 315, with the legs 235 fully deployed on the far side of the blood vessel and the proximal end of distal implant 205 extending into the interior of the blood vessel (FIG. 27). Thus, in the placement of the device the vessel or tissue is pierced (transfixed). Notwithstanding the transfixion, the legs close the vessel or tissue to prevent flow and, therefore, there is no or minimal leakage of blood from the transfixion aperture. This may be contrasted with use of staples or sutures to occlude vessels or clamp tissue in which loss of blood through the puncture holes is a common problem.

Figure 39:
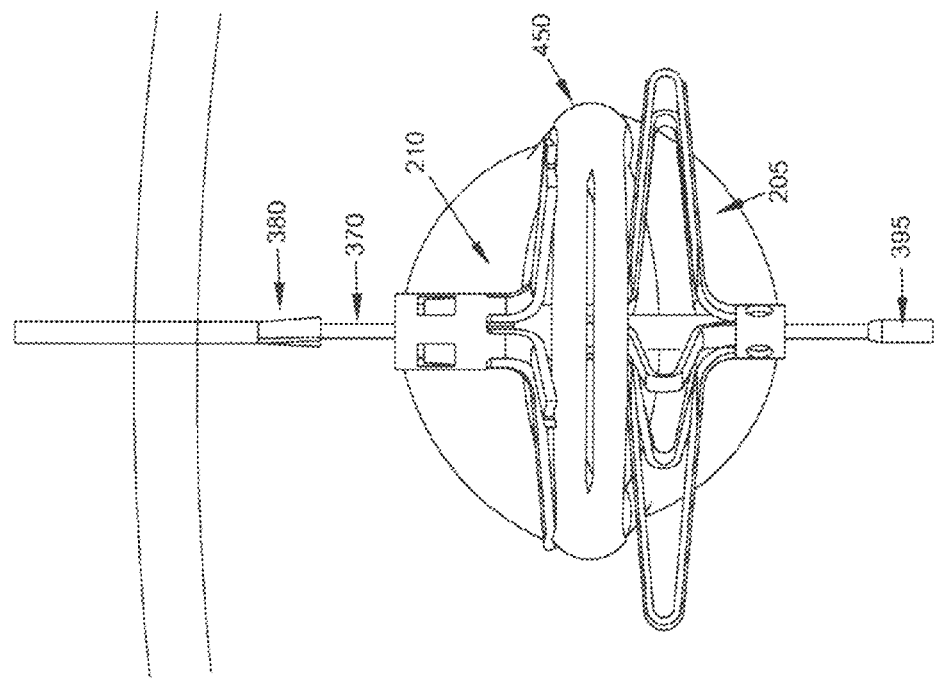
Figure 38:
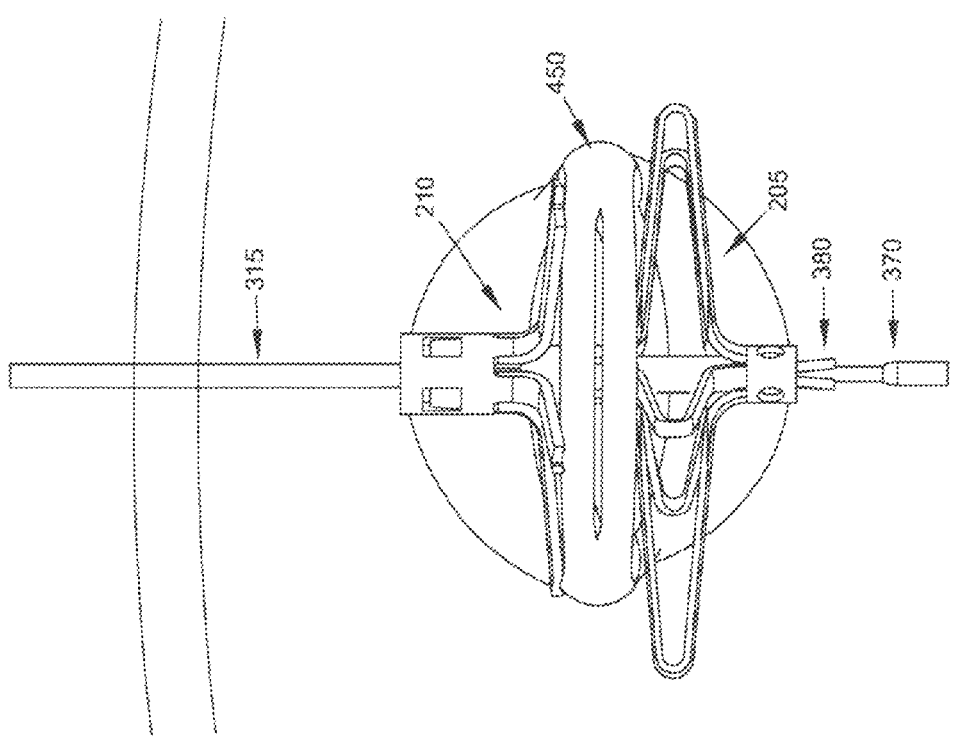
Figure 41:
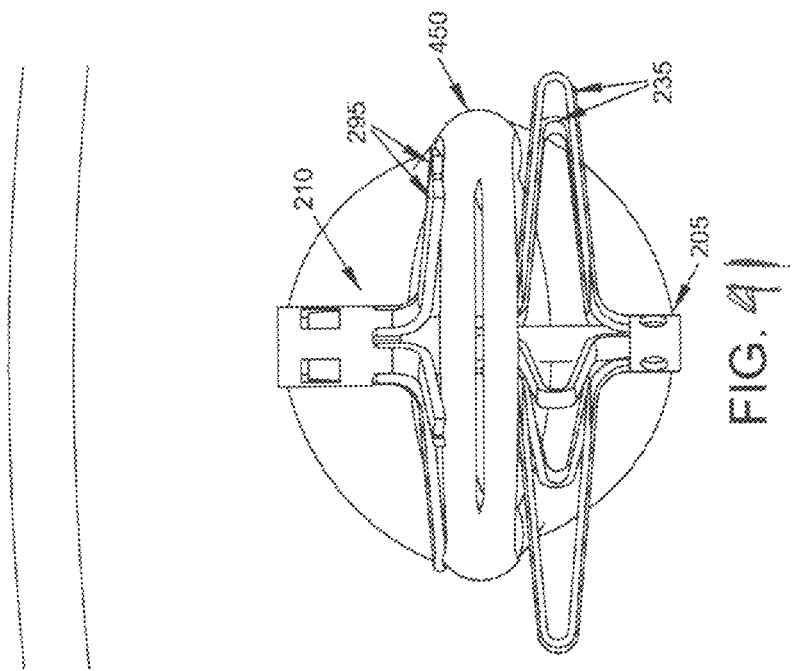
Figure 40:
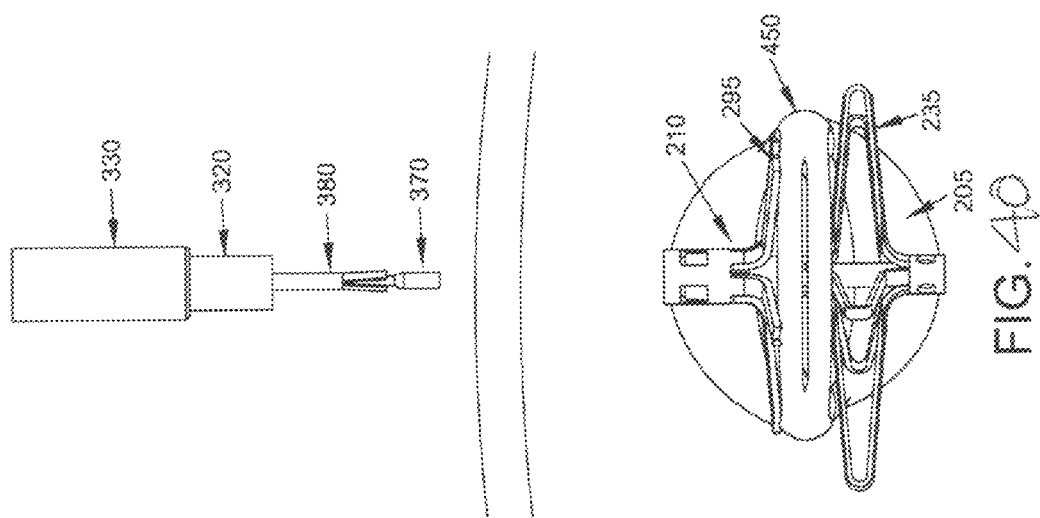

With the distal implant so placed and deployed, the proximal implant delivery tube 330 (carrying proximal implant 210 therein) is advanced over and along composite guidewire 315, until the distal end of proximal implant delivery tube 330 sits just proximal to the blood vessel (FIGS. 28-31). Push rod 320 then is used to advance the distal end of proximal implant 210 out of the distal end of proximal implant delivery tube 330. As this occurs, legs 295 are released from the constraint of proximal implant delivery tube 330 and open radially (FIGS. 32-35). Then, using push rod 320, proximal implant 210 is pushed distally along the guidewire as distal implant 205 is pulled proximally using composite guidewire 315, the distal end of the guidewire sheath 380 being enlarged by enlargement 395. As distal implant 205 and proximal implant 210 are drawn together, their legs 235, 295 cooperate to compress the blood vessel, thereby occluding it. Distal implant 205 and proximal implant 210 continue moving together until inwardly-projecting tangs 300 of proximal implant 210 enter windows 245 of distal implant 205, thereby locking the two together as shown in FIG. 36. At this point push rod 320 and proximal implant delivery tube 330 are removed. See FIG. 37. Next, composite guidewire 315 is removed by first advancing guidewire rod 370 distally (FIG. 38) to enable the sheath to contract to its smaller diameter. to a size smaller than lumen 262 in distal implant locking tube 220. Guidewire sheath 380 and rod then can be withdrawn proximally through the interior of two-part occluder 200 (FIG. 39). The foregoing procedure leaves two-part occluder 200 locked in position across the blood vessel, with the opposing legs 235, 295 compressing the blood vessel, whereby to occlude the blood vessel. It should be understood that the composite guidewire 315 may take other forms that also serve to detachably bind to the distal implant such as, for example, providing threads on the end of the guidewire to cooperate with a threaded recess on the distal implant to connect releasably the distal end of the guidewire to the distal implant.

Figure 42:
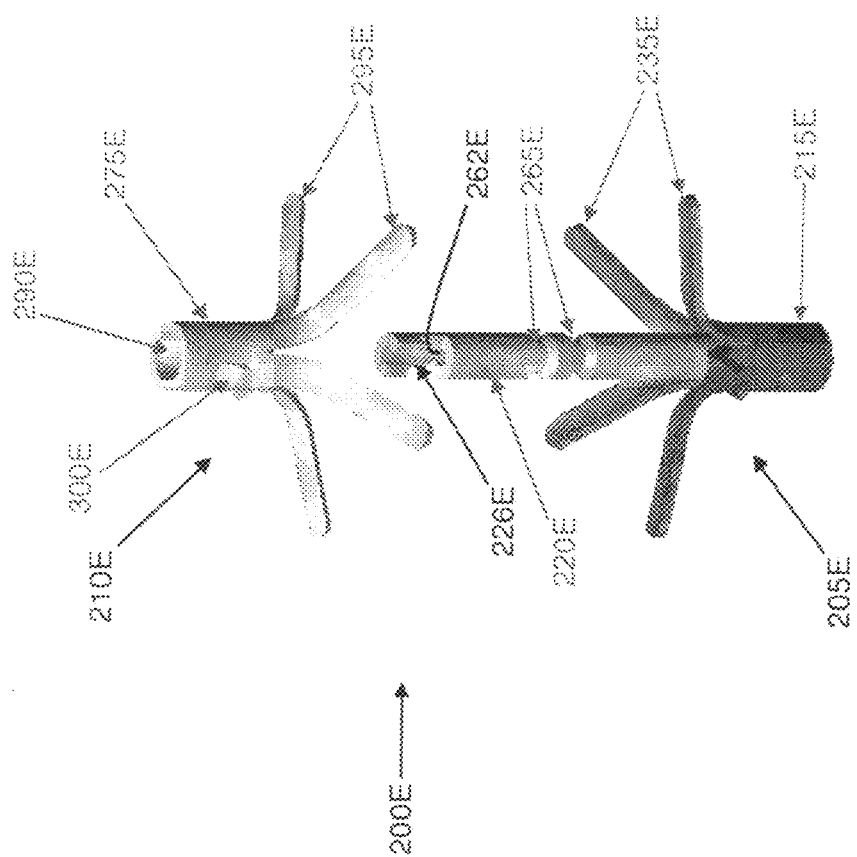
FIG. 42 is an isometric illustration of another embodiment of the invention.

In practicing the invention the legs of one or both of the implants may be arranged to expand generally perpendicular to the axis of the occluder or may be arranged to extend at an acute angle to the longitudinal axis of the implant such that the legs on one or both of the implants collectively define a cone-like concave region (e.g., at 301E in FIG. 44). The angle defined by the cone-like shape is referred to as the "cone angle" and may be varied to provide for different device characteristics. The arrangement may be varied such that when both implants include legs defining the concave regions the concave regions may face each other (FIG. 42) or may face in the same direction (FIG. 46) in a somewhat nesting configuration.

Figure 48:
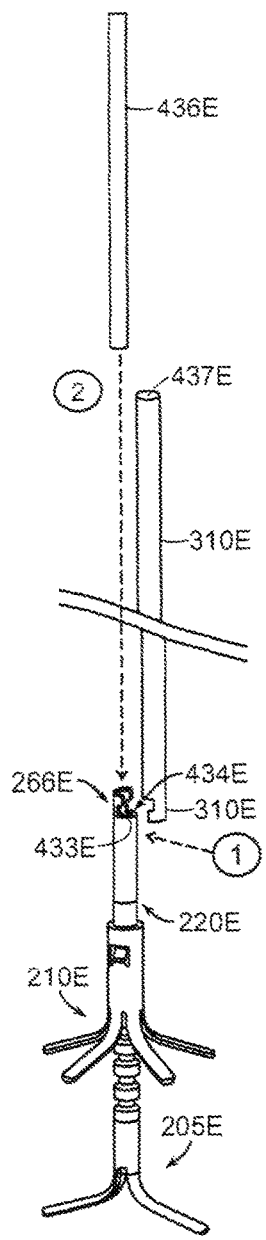
FIGS. 48-50 are sequential illustrations of the manner in which the embodiment of FIGS. 46 and 47 may be employed to deliver and deploy an occluder.
Figure 49:
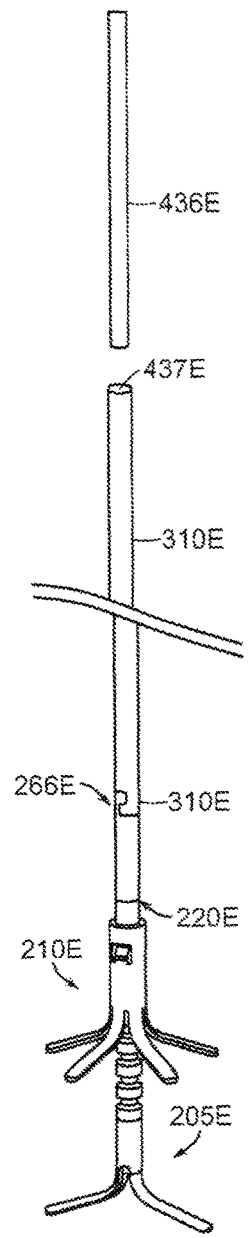
Figure 50:
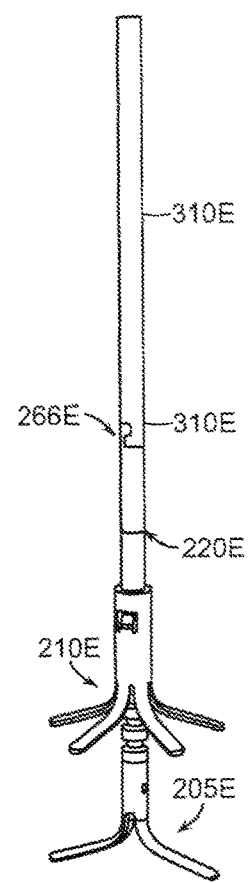

FIGS. 42-45 illustrate another form of the invention embodying an arrangement in which both the distal and proximal implants can be stored in and delivered through the same delivery tube or needle rather than separate proximal and distal implant delivery tubes. Additionally, this embodiment illustrates a separate and alternative arrangement for securing the proximal and distal implants together. In this embodiment locking tube 220E of the distal implant is provided with one or more longitudinally spaced circumferential grooves or recesses 265E formed along its length. As with the previously described embodiment, locking tube 220E is secured at its distal end to the distal end of the distal implant body 215E as by spot welding, adhesives, mechanical interlocks, etc. Instead of the arrangement of a composite guidewire to retain the distal implant, the proximal end of the locking tube 220E also comprises a first half 266E of a mechanical interlock by which the locking tube 220E (and hence distal implant 205E) can be connected to a distal implant retention tube 310E that has a mating second half 361E of the mechanical interlock as described below. The mechanical interlock enables the distal implant to remain attached to the deployment device until the proximal implant has been deployed and secured to the distal implant, as described below. As shown in FIGS. 48-50, the halves of the interlock 266E comprise a stepped configuration 433E, 434E, they being complementary so as to mate together. Although we have found that the connection tends to stay together, a locking rod 436E may be passed through the interlock to further secure the connection. The rod must be removed or withdrawn before separation of the interlock components. Alternatively, internal locking rod 436E may be replaced by an overtube (not shown) which telescopically projects over distal implant delivery tube 310E and distal implant locking tube 220E of distal implant 205E, whereby to enhance the connection between the members.

Locking tube 220E preferably is formed out of the same or similar material as described above. By way of example but not limitation, distal implant locking tube 220E may be formed out of a titanium alloy such as Ti 5 AL-4V or Nitinol.

In the embodiment of FIGS. 42-45 inwardly projecting tangs 300E are formed in tube 275E of the proximal implant for engaging the grooves or recesses 265E in distal implant locking tube 220E. If desired, the locations and configurations of grooves or recesses 265E and tangs 300E can be reversed, i.e., outwardly-projecting tangs 300E can be provided on locking tube 220E and grooves or recesses 265E can be provided on the inner side wall of tube 275E, or other means can be provided for connecting tube 275E of proximal implant 210E to locking tube 220E of distal implant 205E. The positions of circumferential grooves or recesses 265E of locking tube 220E and inwardly-projecting tangs 300E of proximal implant 210E are coordinated so that when they engage legs 235E of distal implant 205E and legs 295E of proximal implant 210E are sufficiently close to ensure adequate clamping of a blood vessel (or other tubular structure) disposed therebetween.

Figure 73:
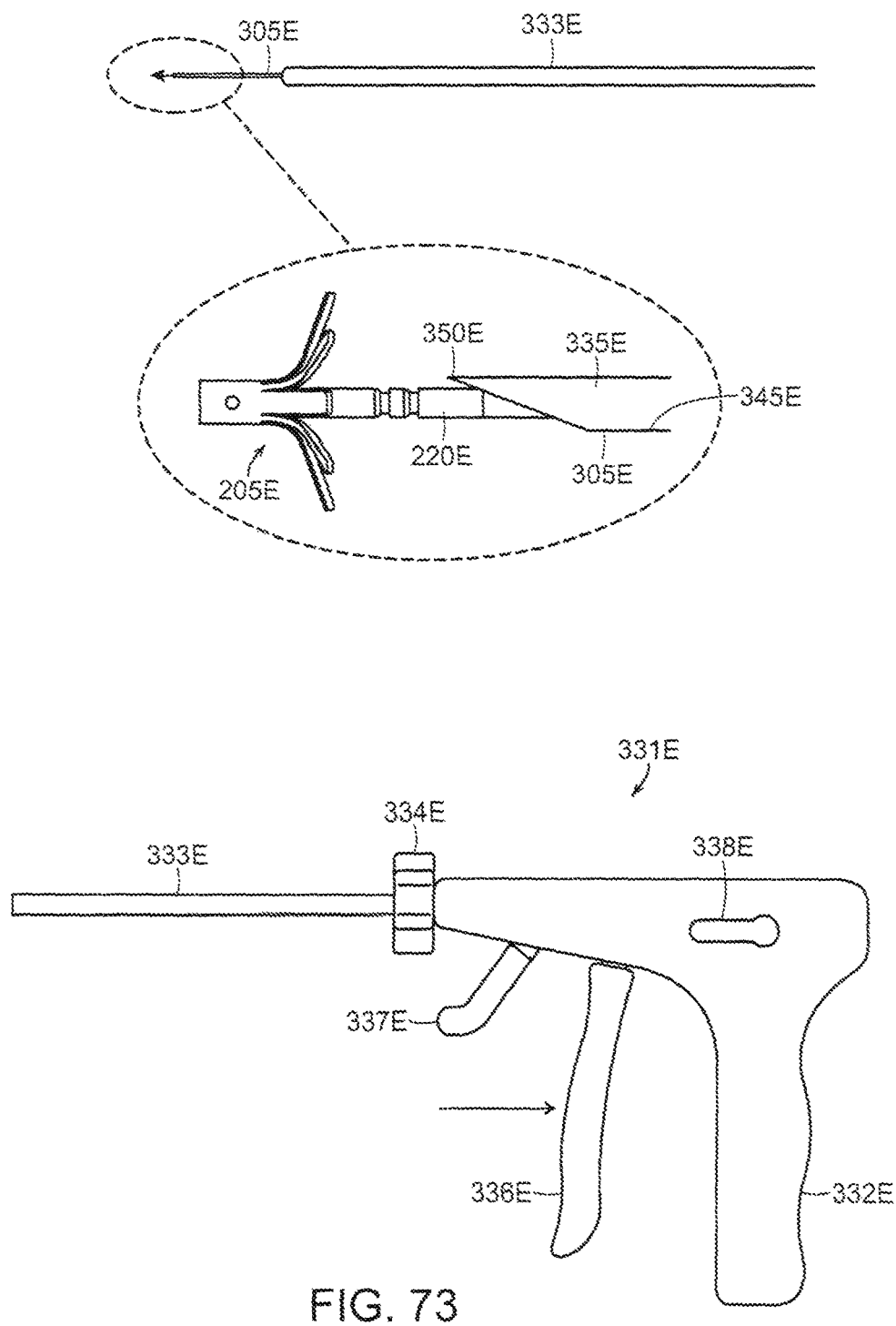
FIGS. 73-77 illustrate the sequential deployment of the embodiment of the occluder of FIGS. 48-50.

The manner in which the occluder 200E may be deployed is illustrated in the context of a laparoscopic procedure using a laparoscopic device 331E. A similar arrangement may be used for percutaneous delivery. First, hollow needle 305E containing both the distal and proximal devices, longitudinally spaced within the needle lumen, is advanced to the occlusion site, for example, while needle 305E is contained within sheath 333E of the delivery device 331E (FIG. 73). In a percutaneous procedure the needle would be inserted directly without a sheath. The spacing between the implants within the needle is greater than the thickness of the vessel or tissue that is to be clamped. Then, sheath 333E is retracted to expose the needle, e.g., by turning knob 334E and the needle 305E is passed transversely through the walls of the blood vessel (e.g., a vein) which is to be occluded or passed through tissue or objects to be secured to one another, such as a solid organ, or layers of tissue, etc. At this point in the procedure, the implants are within the needle but on opposite sides of the vessel or tissue to be clamped. The distal implant is connected, at its mechanical interlock, to the distal end of the distal implant retention tube 310E. The proximal implant is slidably disposed about the distal implant retention tube 310E. Next, hollow needle 305E is retracted proximally, back across the blood vessel, e.g., as by operating first trigger 336E (FIG. 73) to progressively expose the distal implant and to allow legs 235E of distal implant 205E to expand radially on the far side of the blood vessel. The distal implant is held in place by its connection with the retention tube. At this point, distal implant locking tube 220E extends proximally through the blood vessel.

Figure 74:
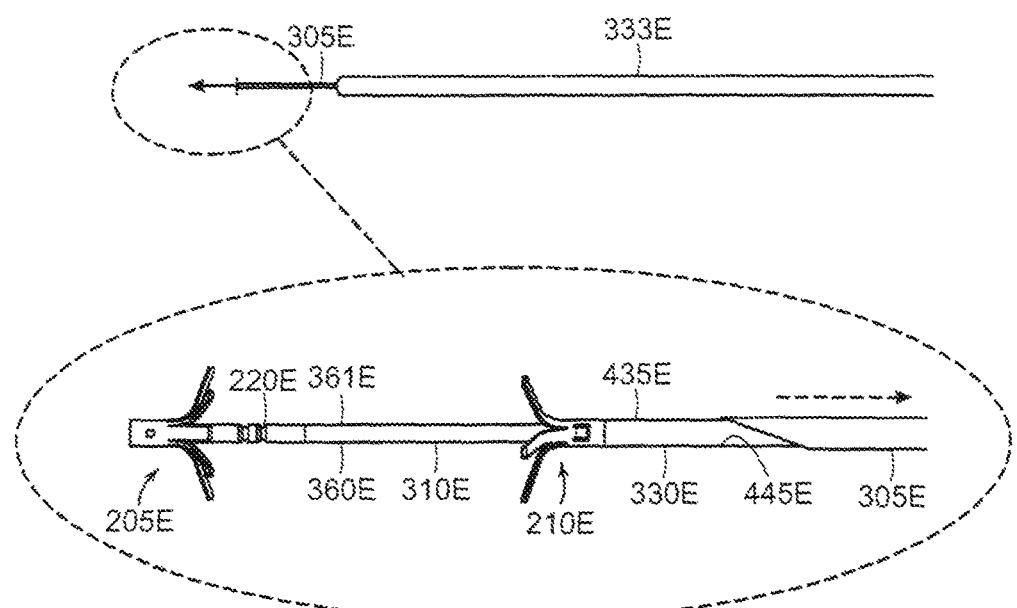

Then, with retention tube 310E held in place, hollow needle 305E is withdrawn further proximally (e.g., via first trigger 336E) until proximal implant 210E is exposed and is no longer constrained within hollow needle 305E (FIG. 74). As this occurs, legs 295E of proximal implant 210E are released fully from the constraint of hollow needle 305E and open.

Figure 75:
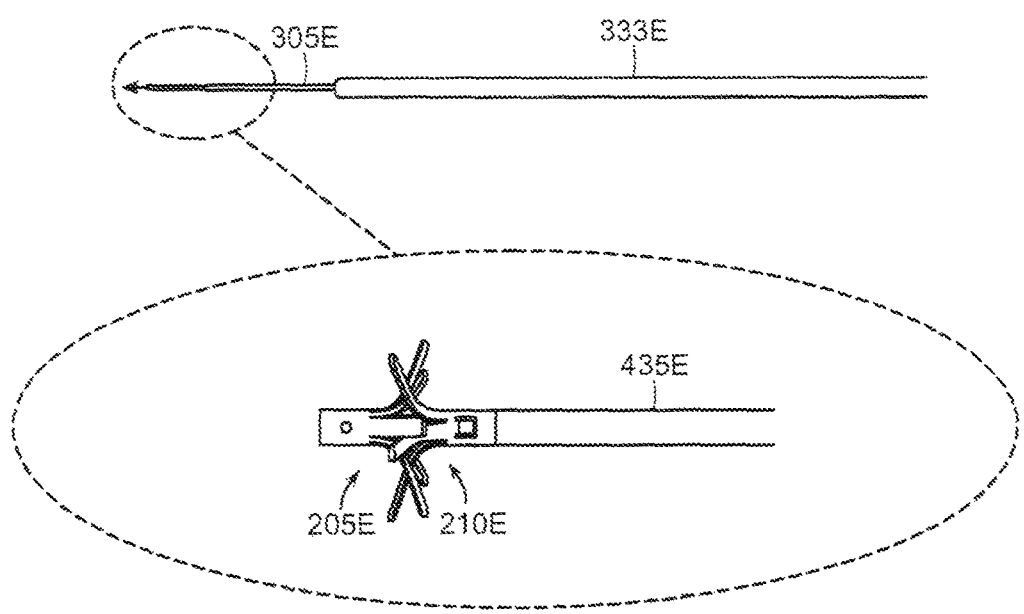
Figure 76:
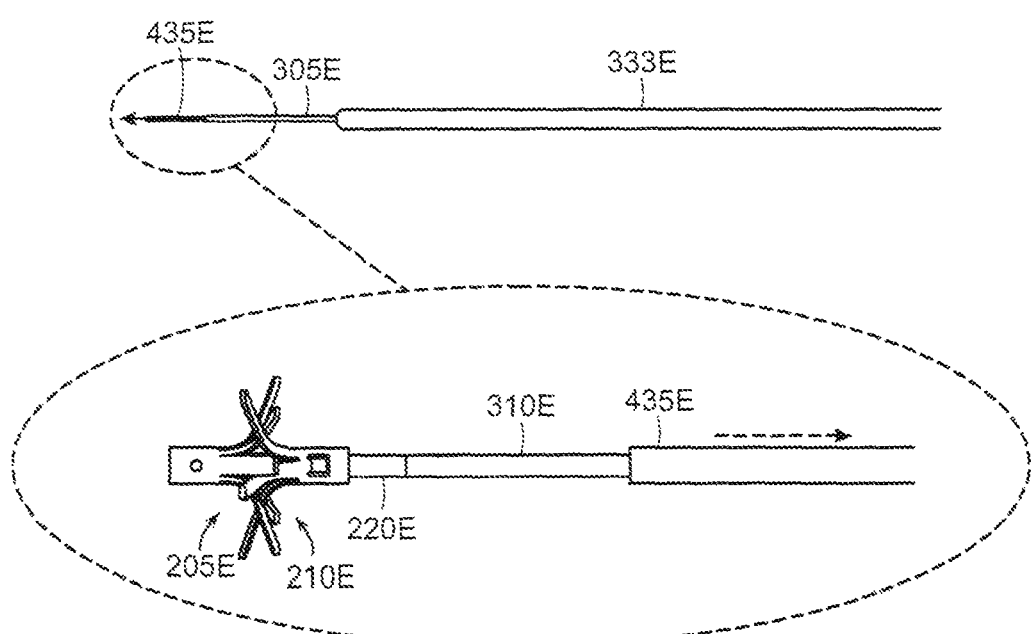
Figure 77:
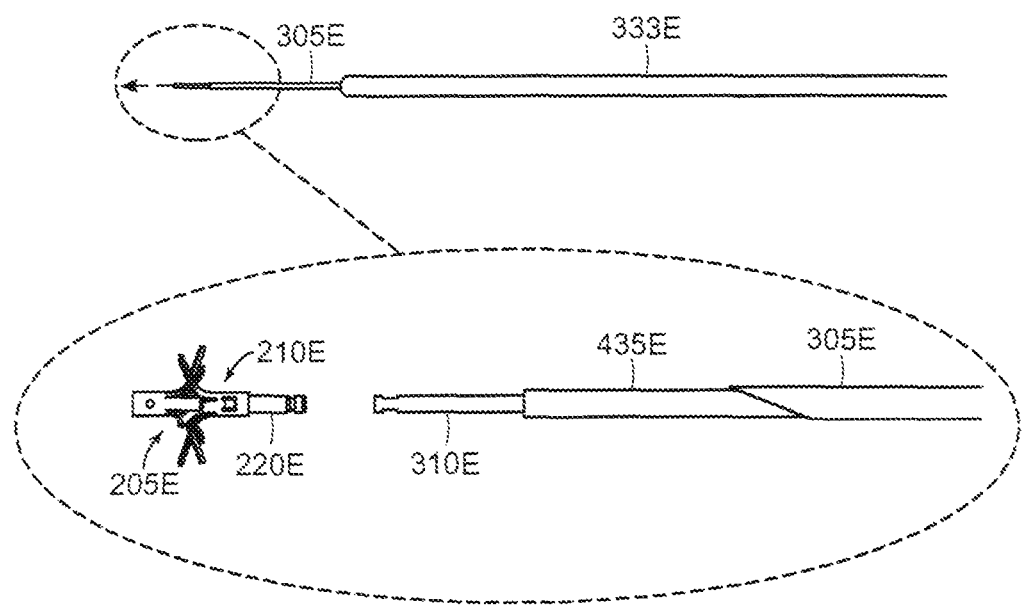

Proximal implant delivery tube 330E then is advanced distally along and about the retention tube 310E, (e.g., using second trigger 337E), to push the proximal implant 210E toward distal implant 205E (FIG. 75). As distal implant 205E and proximal implant 210E are drawn together, their legs 235E, 295E compress the blood vessel therebetween, thereby occluding the blood vessel. Distal implant 205E and proximal implant 210E continue moving together until inwardly-projecting tangs 300E of proximal implant 210E enter circumferential grooves or recesses 245E of distal implant 205E, thereby locking the two members into position relative to one another. Proximal implant delivery tube 330E is withdrawn (FIG. 76), retention tube 310E is released from distal implant 205E (i.e., by using lever 338E) to unlock the second half 361E of the mechanical interlock from the first half 266E of the mechanical interlock, and then the installation device is withdrawn (FIG. 77).

The foregoing procedure leaves two-part occluder 200E locked in position across the blood vessel, with the opposing legs 235E, 295E compressing the blood vessel therebetween, whereby to occlude the blood vessel.

In the preceding disclosure, two-part occluder 200E is discussed in the context of using the elasticity of its legs 235E, 295E to cause its legs 235E, 295E to reconfigure from a diametrically reduced configuration (e.g., when constrained within a delivery needle) to a diametrically expanded configuration (e.g., when released from the constraint of a delivery needle). However, it should also be appreciated that where legs 235E, 295E are formed out of a shape memory material (e.g., Nitinol), a temperature change may be used to reconfigure legs 235E, 295E from a diametrically-reduced configuration to a diametrically-expanded configuration. By way of example but not limitation, in this form of the invention, legs 235E, 295E may be constructed so as to have a diametrically reduced configuration when maintained at a temperature below body temperature, and legs 235E, 295E may be constructed so as to have a diametrically expanded configuration when maintained at body temperature. As a result, by cooling two-part occluder 200E to a temperature below body temperature, inserting the two-part occluder into the body, and then allowing the two-part occluder to heat to body temperature, legs 235E, 295E can be caused to reconfigure from their diametrically-reduced configuration to a diametrically-expanded configuration.

Although the system has been described primarily in connection with a percutaneous delivery device, the installation apparatus can be adapted for use in laparoscopic, endoscopic or open surgical procedures, as by associating the components of the delivery system (a hollow needle, distal implant delivery tube, a composite guidewire or equivalent, a tubular push rod and a proximal implant delivery tube) with an appropriate handle at the proximal end of the system for controlling the operation of the components.

Although the two-part occluders discussed above rely on the superelasticity of the material to cause the legs of the implants to self-expand when released from the delivery tube, it should also be appreciated that where legs 235E, 295E are formed out of a shape memory material (e.g., Nitinol), a temperature change may be used to reconfigure legs 235E, 295E from a low profile, diametrically reduced configuration to a diametrically expanded configuration. By way of example but not limitation, in this form of the invention, legs 235E, 295E may be constructed so as to have a diametrically reduced configuration when maintained at a temperature below body temperature but to have a diametrically expanded configuration when maintained at body temperature. As a result, by cooling two-part occluder 200E to a temperature below body temperature, inserting the two-part occluder into the body, and then allowing the two-part occluder to heat to body temperature, legs 235E, 295E can be caused to reconfigure from their low profile, diametrically reduced configuration to a diametrically expanded configuration.

Figure 46:
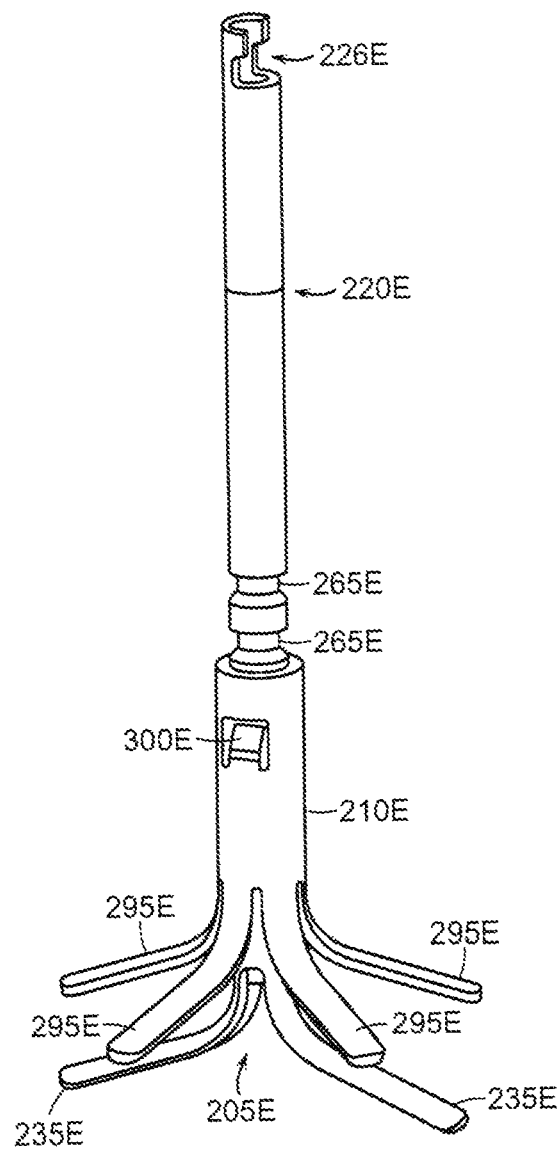
FIG. 46 is an isometric illustration of another embodiment of the invention.
Figure 47:
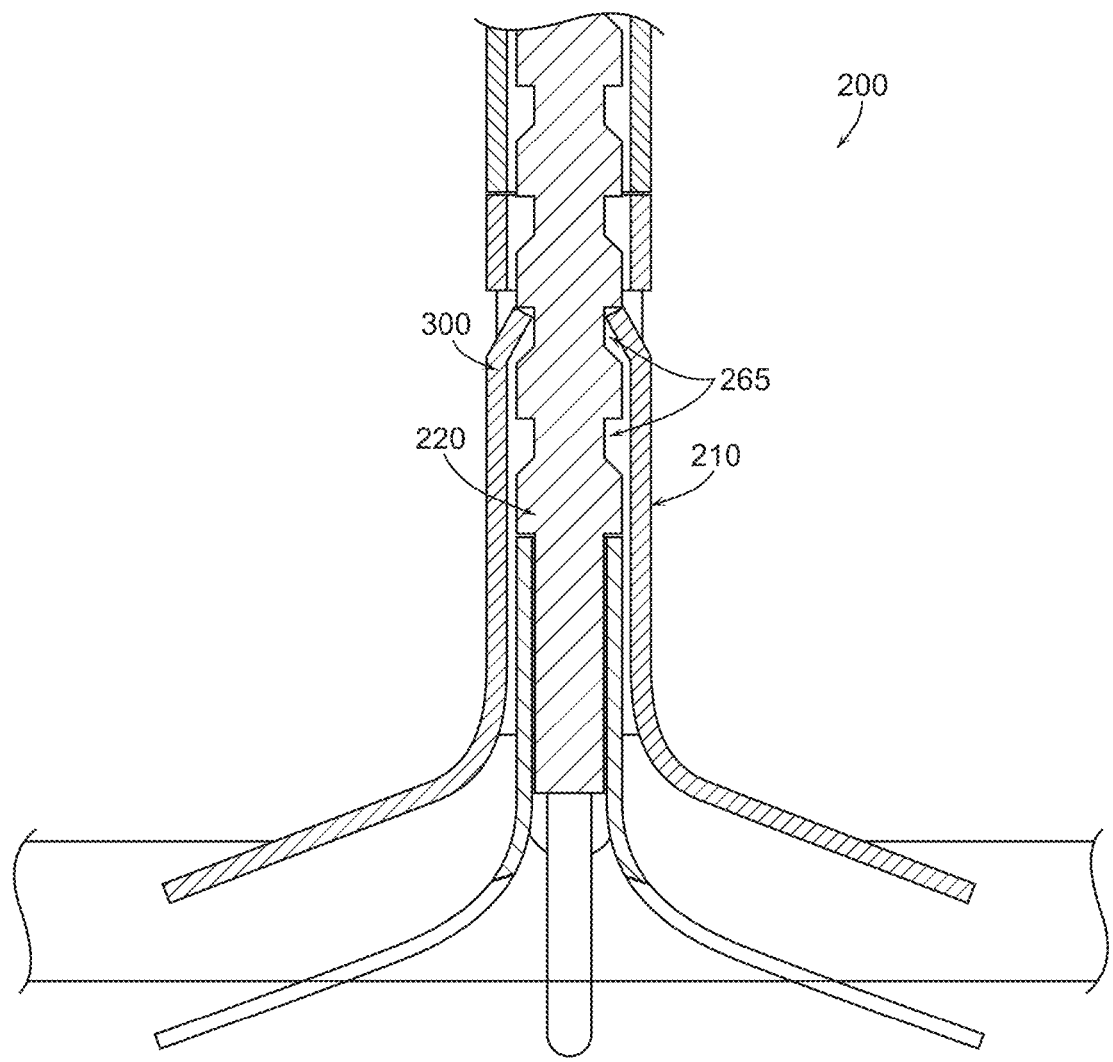
FIG. 47 is a longitudinal sectional illustration of the embodiment of FIG. 46 showing a ratcheting mechanism incorporated in the occluder.

FIG. 46-47 show another two-part occluder 200E similar to that described above except that legs 235E of distal implant 205E, and legs 295E of proximal implant 210E, have their concavities facing in the same direction, so that legs 235E, 295E nest with one another rather than confront one another. In addition, as seen in FIGS. 46-47, tube 225E of distal implant 205E is partially received in lumen 290E of proximal implant 210E.

FIGS. 48-50 illustrate the releasable mechanical interlock for connecting the distal implant to distal implant retention tube 310E. As shown in FIGS. 48-50, the first half 266E of the mechanical interlock carried by the proximal end of locking tube 220E comprises a stepped configuration 433E, and the second half 361E of the mechanical interlock carried by the distal end of distal implant delivery tube 360E comprises a mateable, complementary stepped configuration 434E. With the complementary parts engaged, the connection may be secured by placing a locking rod 436E through central lumen 437E of distal implant retention tube 310E and into lumen 262E of implant locking tube 220E. Alternatively, in another form of the invention, internal locking rod 436E may be replaced by an overtube (not shown) that can be placed over the engaged distal implant retention tube 310E and locking tube 220E to prevent, temporarily, their separation.

It should also be appreciated that other forms of temporary mechanical interlocks may be used for releasably securing distal implant 205E of the two-part occluder 200E of FIGS. 46 and 47 to distal implant retention tube 310E. By way of example but not limitation, a screw interlock may be used, e.g., the first half 266E of the mechanical interlock (carried by the proximal end of distal implant locking tube 220E) may comprise a threaded bore, and the second half 361E of the mechanical interlock (carried by the distal end of distal implant delivery tube 360E) may comprise a threaded post, wherein the threaded post carried by the distal end of distal implant delivery tube 360E may be received in the threaded bore of distal implant locking tube 220E. Alternatively, other configurations of a screw interlock may be used, or other forms of mechanical interlocks may be used. In still another variation the locking tube 220E can be formed integral with distal implant retention tube 310E, with a weakened section disposed at their intersection, and with the two members being separable a mechanical breaking action.

Figure 51:
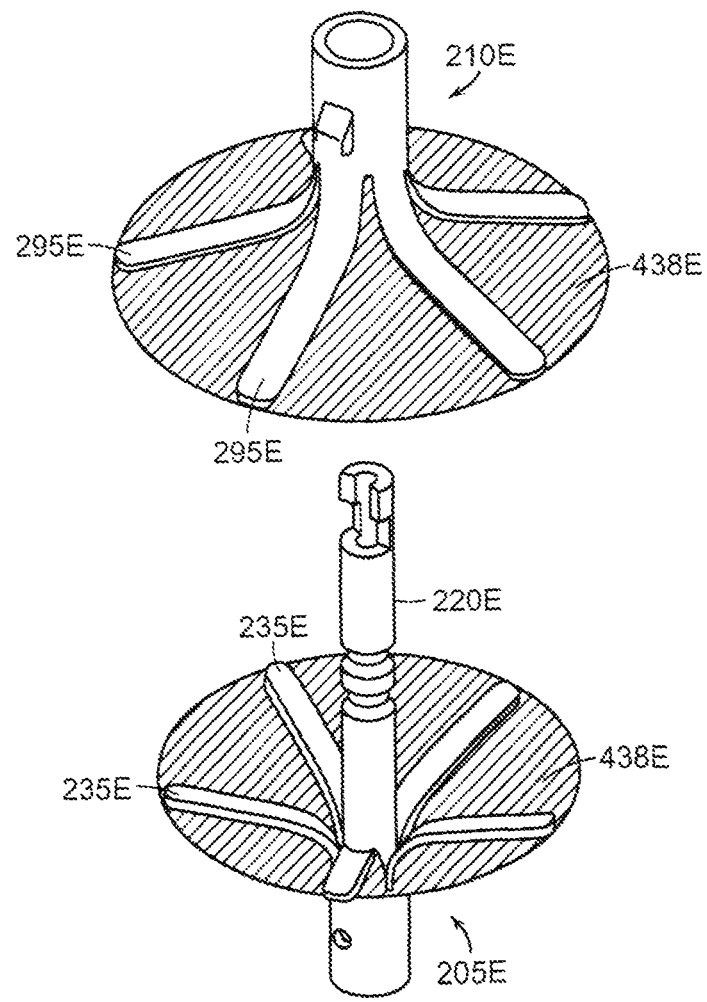
FIG. 51 is a diagrammatic illustration of an occluder in which webbing is carried by the legs of the implants.

It will be appreciated that, in certain circumstances, it may be desirable to increase the surface area of those portions of the occluder that contact the tubular body structure, in order to better distribute the load applied to the tissue. In this situation, it can be helpful to increase the width of the legs (e.g., legs 235E and/or legs 295E of two-part occluder 205E, etc.), and/or to provide flexible material in the zone between adjacent legs (e.g., in the manner of an umbrella) so that the flexible material can also carry load (i.e., essentially increasing the effective width of legs 235E and/or legs 295E). See, for example, FIG. 51, which shows flexible material 438E extending between legs 235E and legs 295E.

The relative orientation of the legs of the proximal and distal implants may be selected to provide different clamping patterns, the selection of which may depend on the particular anatomy and characteristics of the tissue with which it is to be used. In one configuration, as described above and as shown diagrammatically in FIGS. 52A and 52B, the legs 295 of the proximal implant are arranged to be in registry with some or all of the legs 235 on the distal implant such that pairs of proximal and distal legs 295, 235 will cooperate to directly compress the vessel or other tubular body structure or tissue along a series of angularly spaced, radial extending clamping lines CL as suggested diagrammatically in FIG. 52. It may be noted that although the direct clamping tends to cause the opposing walls of the vessel to contact each other between the clamping lines as well as along the clamping lines CL, in some cases direct contact may not occur in one or more regions between the clamping lines CL. However, even where some such regions may exist, the arrangement of multiple, angularly spaced direct clamping lines provide enough obstruction to the lumen to cause effective occlusion.

FIGS. 53 and 53A illustrate another arrangement of the legs 295, 235 of the proximal and distal implants in which the legs are interdigitated so that they do not effect a direct clamping of the tissue but, instead, engage the tissue to constrain the tissue in a serpentine configuration extending at least partly about the axis of the occluder in a generally circumferential direction. In an interdigitated arrangement, the legs of one of the implants are out of registry with those of the other implant so that when viewed in plan, the legs of one implant lie between the legs of the other. In particular, arranging the legs in an interdigitated array is considered to allow a tubular structure to be safely occluded in a way that avoids leakage problems associated with staples or conventional clips (e.g., hemoclips, Ligaclips, etc.). In an interdigitated configuration the opposing walls of the vessel are together partially wrapped about the legs in alternating directions to constrain the tissue in a serpentine configuration as seen diagrammatically in FIG. 53A. Additionally, interdigitation provides an additional means by which the clamping forces can be adjustably controlled. By selecting a particular cone angle defined by the expanded legs, coupled with the dimensions and positioning of the mechanical locking mechanism by which the relative position of the legs of the deployed occluder are determined, the characteristics of the serpentine pattern can be determined. Cone angle selection also may be used to control the degree of compression between the legs of the implants in the direct clamping embodiment of FIGS. 52, 52A.

FIG. 54 shows a two-part occluder 200 and illustrates further the manner in which the legs 295 of the proximal implant 210 are interdigitated with the legs 235 of the distal implant 205. When interdigitated, the outer free ends of the legs of each, in the absence of engaged tissue, intersect a plane defined by the free ends of the other, a condition that may be referred to as "overlap". If desired, the degree of overlap (and, therefore, the degree of interdigitation) may be designed into the device by selecting the cone angle for the legs and the location of the locking mechanism for the implants.

Another variable that may be used to control the manner in which the occluder engages the tissue is to vary the angular offset between the legs of the proximal and distal implants. Variable offset between legs 235 and legs 295 allows for the adjustment of clamping tension applied to the tissue. For example, for delicate or easily damaged or torn tissue (e.g., brain tissue), or tissue that has limited elasticity, it is believed to be generally preferable that legs 235 and legs 295 are out of alignment to constrain the tissue in serpentine pattern (interdigitation) so that no direct compression is applied to the tissue. The cooperative tangs and windows or detents and grooves 265 may be arranged to provide for a selected degree of overlap and interdigitation. In the arrangement of tangs and windows there may be one or several circumferentially spaced windows by which the angular orientation of the legs of the implants can be varied when locked.

Figure 55:
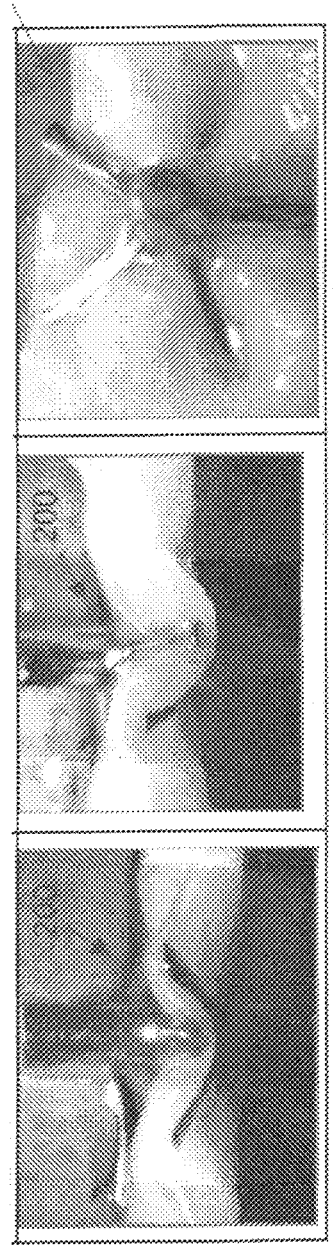
FIG. 55 is a series of three photographs of a tubular vessel showing how the occluder with interdigitated legs constrains the vessel to occlude it.

FIG. 55 shows three photographs of a two-part occluder 200 with interdigitated legs effectively clamping a simulated blood vessel. The interdigitated legs cause serpentine ripples, or folds, in the tissue that act to extend the effective closure, and causes closure of the vessel well beyond the region directly contacted by the occluder legs 235, 295. This is believed to result because the serpentine pattern extends radially somewhat beyond the periphery defined by the implant legs. By way of example but not limitation, a two-part occluder 200 having a physical occlusion diameter of 5.5 mm is able to close vessels that are over 7 mm (and even equal or greater than 1 cm) in diameter.

It should be understood that when an interdigitated device is locked into engagement with tissue, the thickness or nature of the tissue may cause the legs to flex to an extent that the degree of overlap is reduced or the legs may no longer overlap at all. Even when this occurs the legs of the proximal and distal implants still apply forces to the tissue that alternate in proximal and distal directions with the legs of the proximal implant applying distally directed forces and the legs of the distal implant applying proximally directed forces. These opposed forces of the implant legs, applied alternately at circumferentially spaced locations about the center of the occluder, are effective to secure tissue layers together or to occlude a lumen.

Additionally, we have found that even when the legs of the proximal and distal implants are initially in registry, when the implants are urged together and locked in very close proximity to each other, the initially registered legs can flex into a non-registered configuration in which the legs may be interdigitated and/or may apply oppositely directed forces to the tissue at circumferentially spaced locations about the center of the occluder as described above, The legs 295, 235 of the proximal and distal implants 210, 205 may be beveled (or rounded) so that they do not present sharp edges, and legs 295, 235 may be designed to separate slightly from the tissue at the free end of each leg. This is in order to minimize any catching or damage that may be imparted on the tissue by legs 235, 295, whereby to minimize tearing or ripping of the tissue. In other embodiments of the present invention, it may be desirable to provide sharp features to legs 235, 295 so that legs 235, 295 catch or pierce the tissue for better gripping. Legs 235, 295 may be provided with smooth surfaces or may be roughened, as by chemical etching or mechanical means, so as to enhance the imaging reflectivity of the implants, or to provide increase tissue capture and gripping.

The two-part occluder as described may be configured to occlude blood vessels under fluid pressures of at least 100 mm Hg and up to 300 mm Hg. Occluders also may be made that are capable of resisting pressure of over 700 mm Hg.

Figure 56:
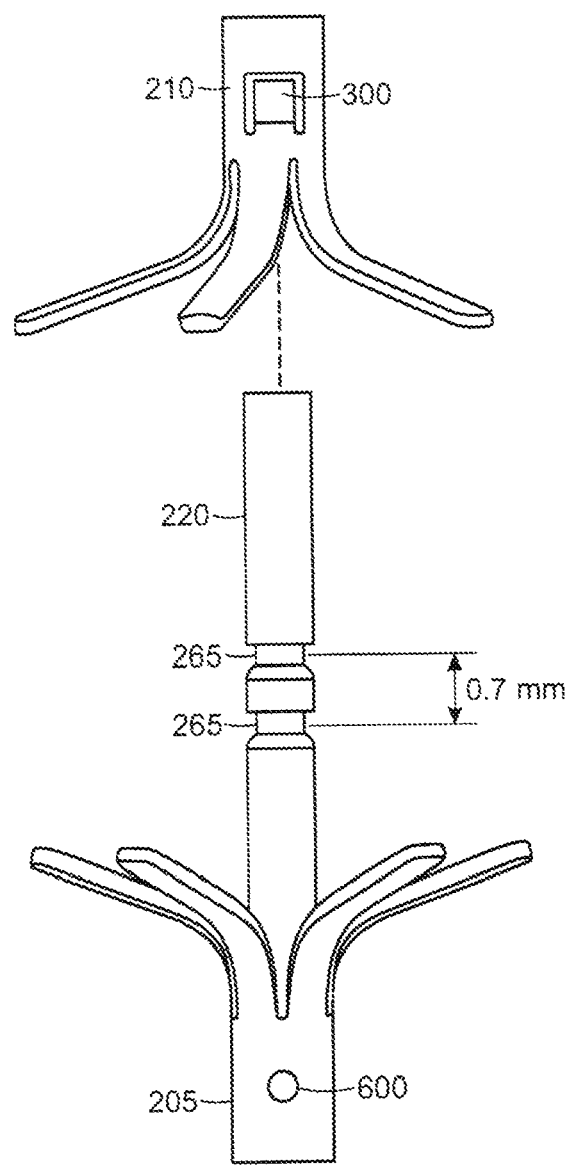
FIG. 56 is another illustration of an occluder showing a ratcheting mechanism.

FIG. 56 shows one embodiment of the present invention wherein distal implant locking tube 220 comprises a controllable ratcheting mechanism for selectively controlling the spacing between proximal implant 210 and distal implant 205 when they are secured together. In this form of the invention, legs 235 of distal implant 205 and legs 295 of proximal implant 210 may be generally oriented primarily in a parallel registered orientation to each other. In this form of the invention, locking tube 220 comprises a plurality of windows 265 (or circular grooves) formed along its length. Proximal implant 210 comprises one or more inwardly projecting tangs 300 formed at a point along its length. As proximal implant 210 is advanced distally towards distal implant 205, inwardly projecting tangs 300 enter into windows 265, thereby locking proximal implant 210 to distal implant 205. Inwardly projecting tangs 300 are configured so that proximal implant 210 can only move in a single direction (i.e., distally) relative to distal implant 205. As proximal implant 210 is advanced distally relative to distal implant 205, inwardly projecting tangs 300 can slide out of windows 265 and enter the next distal window 265. If desired, windows 265 may comprise a chamfered distal edge to facilitate movement of inwardly projecting tangs 300 out of windows 265 as proximal implant 210 moves distally relative to distal implant 205. FIG. 56 shows another variation in which the "notch-to-notch distance" (i.e., the distance between windows 265) governs the ability to vary the degree of compression established between legs 235 of distal implant 205 and legs 295 of proximal implant 210.

Figure 58:
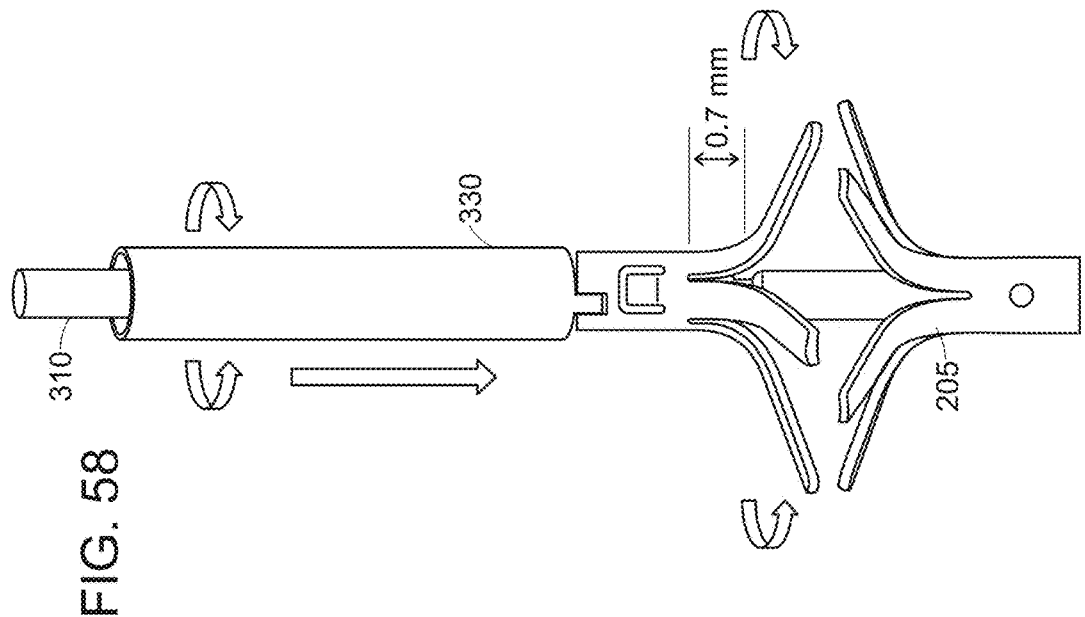
FIGS. 57 and 58 illustrate an occluder and the manner in which the relative angular orientation of the proximal and distal legs can be adjusted.
Figure 57:
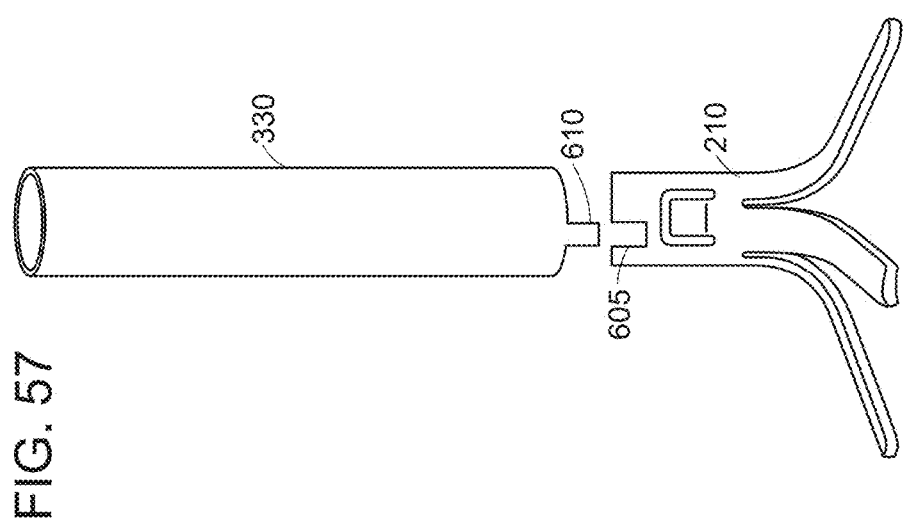

FIGS. 57 and 58 illustrate the a manner in which the rotational orientation of the proximal and distal implants and, therefore, their respective legs may be set. In the example shown, one or more alignment grooves (or notches) 605 may be formed in the proximal end of proximal implant 210, and one or more corresponding orientation alignment post (or tab) 610 may be formed in the distal end of the pusher tube for selective engagement with the grooves or notches 605. The relative orientation of the proximal implant 210 and the distal implant 205 thus can be varied by selectively engaging the grooves and posts and rotating the proximal implant relative to the distal implant until the desired angular orientation is achieved. The procedure can be done under visualization as described above. Alternately, the relative orientation may be adjusted by using the retention tube to rotate the distal implant relative to the proximal implant.

In another modification, the orientation of the legs can be predetermined by providing a slot and groove arrangement between the proximal and distal implants to assure that they can be locked together only in a desired relative angular orientation. Thus the disposition of legs 235 of distal implant 205 relative to the disposition of legs 295 of proximal implant 210 may be controlled so as to apply a desired clamping force according to the type and/or condition of the tissue that is to be clamped.

Figure 59:
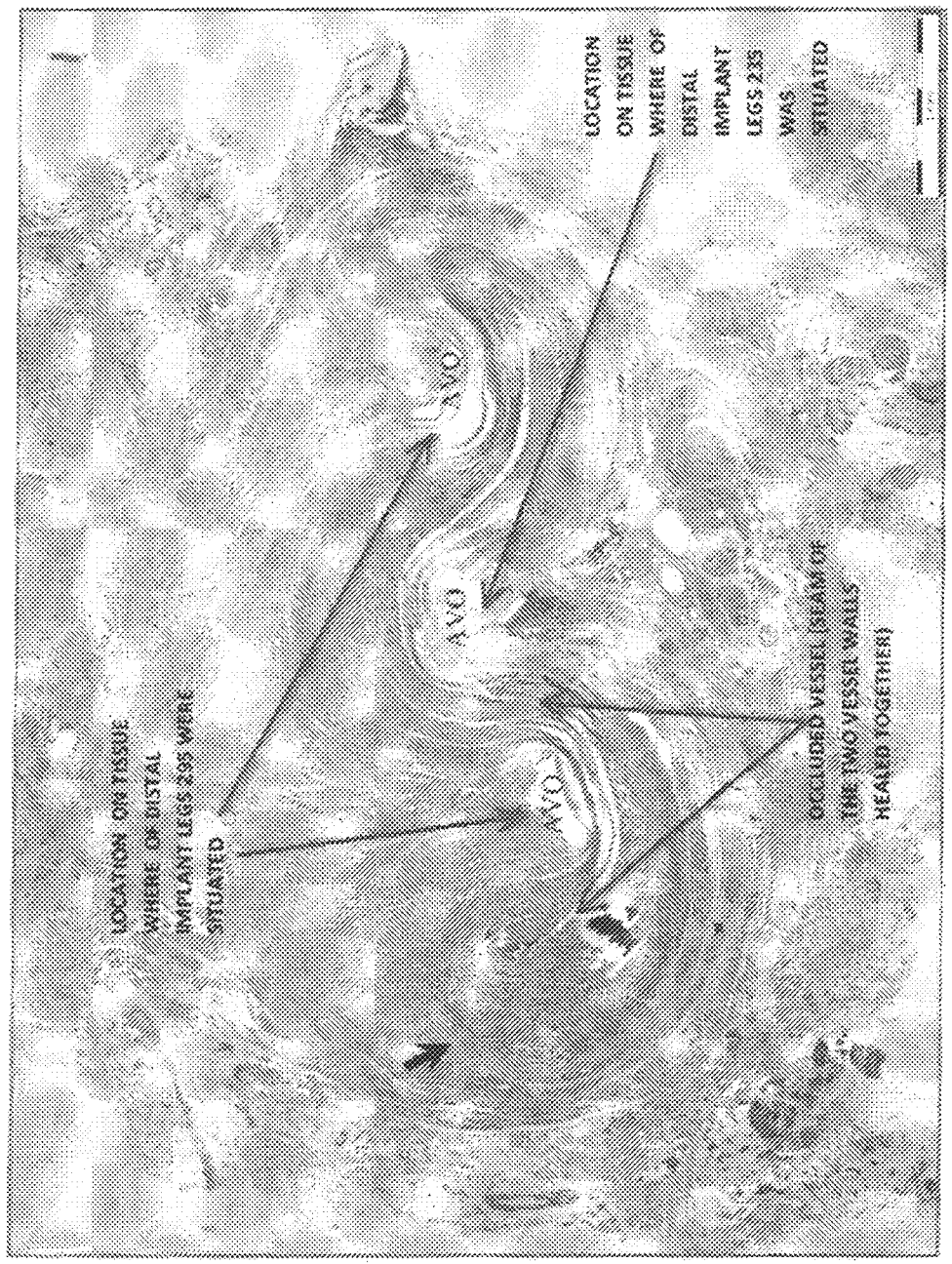
FIG. 59 is a photograph of a histological section of a blood vessel illustrating the manner in which the vessel has been occluded by an interdigitated occluder and after healing.

When the two-part occluder is arranged with its legs interdigitated, the wall thickness of the vessel to be occluded or the tissue layers to be joined does not necessarily determine whether an effective occlusion or attachment can be achieved. As long as the interdigitation of the legs constrains the vessel walls in a serpentine pattern or the forces are alternately applied in proximal and distal directions circumferentially about the center of the occluder the walls of the vessel will may be brought into contact with each other sufficiently to occlude the vessel, even when the legs 235 and legs 295 may not cross each other's plane ("overlap") regardless of the summed wall thickness of the vessel. Thus, vessels, of varying dimensions can be effectively occluded. Whether and to what extent the legs of the proximal and distal implants may overlap will depend on the characteristics and dimensions of the anatomy to be occluded and the configuration for the implants necessary to constrain the tissue in a serpentine configuration.

Where legs 295, 235 of the proximal and distal implants 210, 205 are interdigitated, the serpentine constraint of the tissue layers reduces the force needed to occlude the vessel and is considered to be much less than the force needed to close the same vessel with a conventional ligation clip. FIG. 59 is a photograph of a histological section of tissue from a vessel occluded with an interdigitated occluder and showing the serpentine pattern of the tissue layers of the vessel walls after healing of up to 30 days. The vessel is completely occluded and the vessel wall tissue is compressed and adhered to itself in the serpentine configuration. The "pie crust" or serpentine closure may be observed more clearly as well. The arrow indicates the collapsed undulating artery. AVO indicates the location of the interdigitating legs of two-part occluder 200.

The two-part occluder 200 of the present invention may be used to occlude vessels, ducts and/or to compress tissue so it is occluded/compressed at forces less than 700 grams, while the force required to seal off vessels or clamp tissue with a commercially available Ligaclip are about ten times greater. The two-part occluder 200 of the present invention can maintain operation within the range of elasticity of the material and does not need to be plastically deformed to realize occlusion.

It will be appreciated that the occluder of the present invention can also be used to occlude tubular and hollow structures other than blood vessels. By way of example but not limitation, the temporary occluder of the present invention can be used to occlude fallopian tubes, vas deferens, ducts, as the bile duct and cystic ducts for cholecystectomy, lymphatic vessels, including the thoracic duct, fistula tracts, etc. The present invention can also be used to bring, attach and/or connect at least two folds (e.g., two sides of the stomach, or other parts of the legs, etc.) together so that they are connected.

Figure 60:
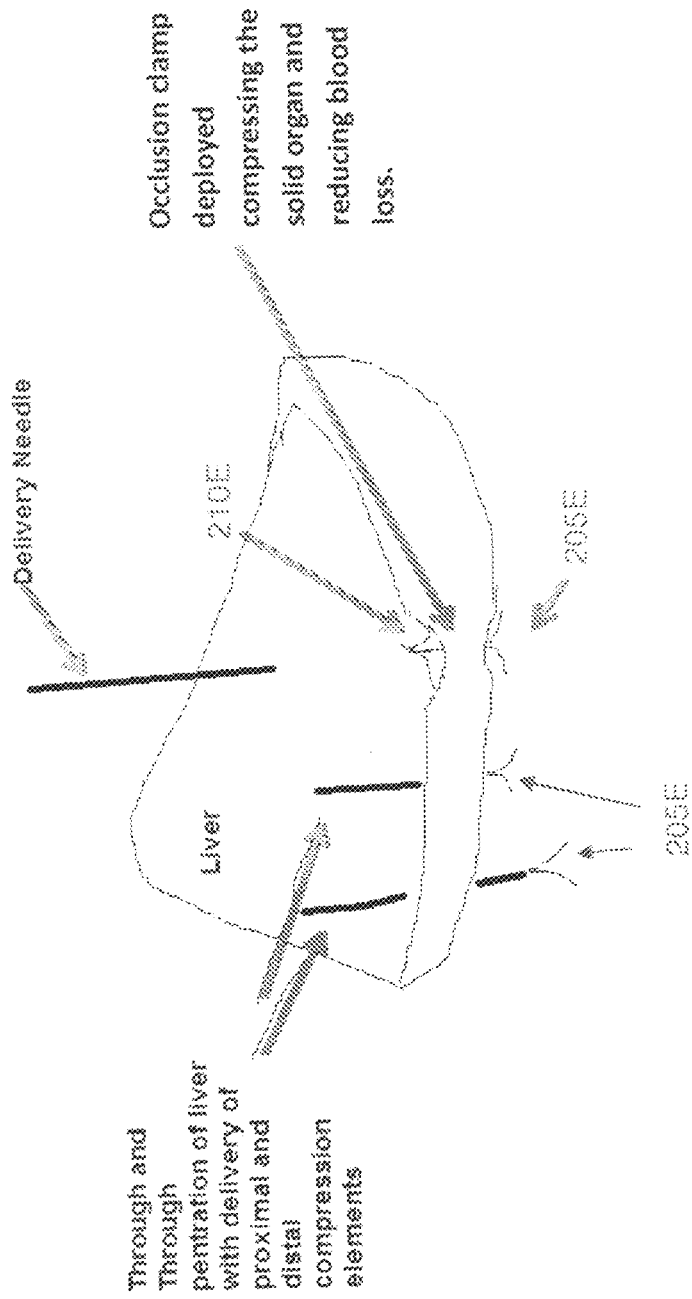
FIG. 60 illustrates, diagrammatically, multiple, single, separate puncture placements of occluders for closing off a resected liver.

In addition to occluding blood vessels the occluders can be used for clamping and compressing regions of resected organs so as to reduce or stop blood flow or blood loss after surgery. For example, as shown in FIG. 60 the occluder may be used in solid organ resection of the kidney or liver or other organs. Blood loss and secretion leakage (e.g., bile, urine, etc.) can be problematic in existing solid organ resection procedures. Average blood loss for a liver resection is 700-1200 ml. By clamping desired regions of the solid organ with one or more occluders, it is possible to significantly reduce the amount of undesirable fluid loss (blood loss, secretion leakage, etc.). The occluder can be used to apply pressure selectively to broad areas of the organ and, additionally, may also be used to close off selective tubular structures and vessels connecting the organ with other regions of the body. Multiple discrete occluder elements may be deployed across regions of the organ as suggested in FIG. 60. Where multiple, single, separate puncture placements of the occluder are used, different regions of the solid organ may be compressed to different and controllable degrees.

Although described in the context of occluding blood vessels, the present invention may be practiced under direct visualization (e.g., during "open" surgery) or under indirect visualization (e.g., during laparoscopic surgery where visualization is provided through the use of a scope, or during percutaneous surgery where visualization is provided through the use of imaging apparatus such as an ultrasound imager, an X-ray imager, etc.).

The present invention can be used for occlusion of tubular structures such as veins, arteries, bile ducts, fallopian tubes, cystic ducts, etc.

The present invention can also be used to connect tissue with other materials, e.g., graft materials, hernia meshes, drug delivery materials, etc.

Figure 61:
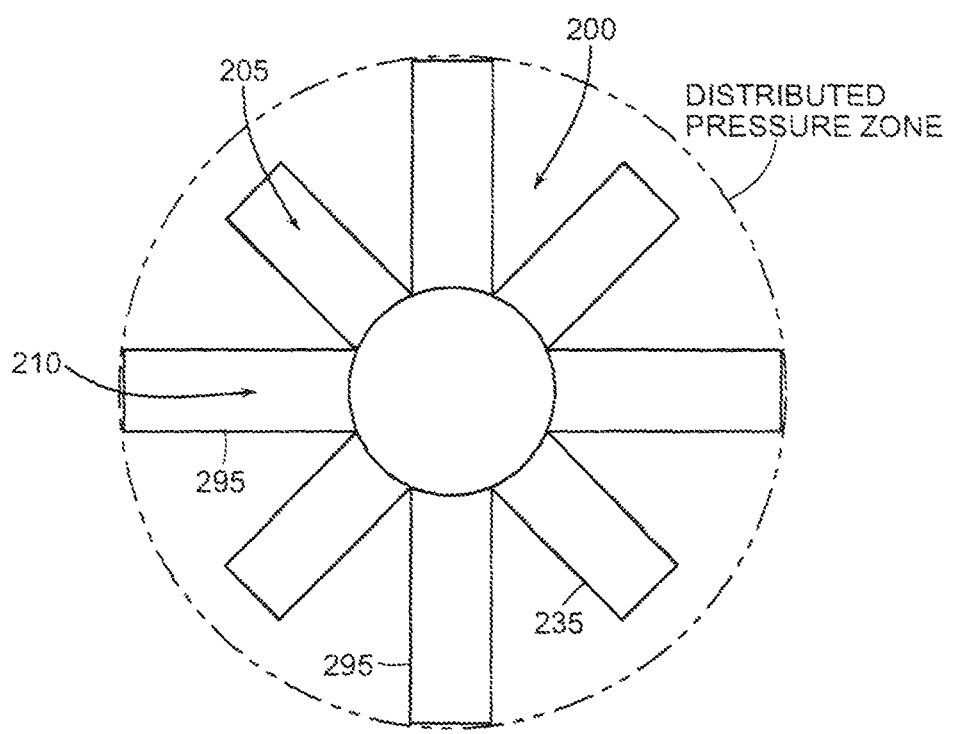
FIG. 61 Is a diagrammatic plan view of an occluder in which some of the legs are wider or longer than others.

FIG. 61 shows a two-part occluder 200 and its surrounding effective pressure zone. Note that the different overlaps between legs 295 of proximal implant 210 and legs 235 of distal implant 205 are controllably adjustable to provide the desired pressure zone and occlusion level. The legs also may be formed to have different and varying widths.

Figure 62:
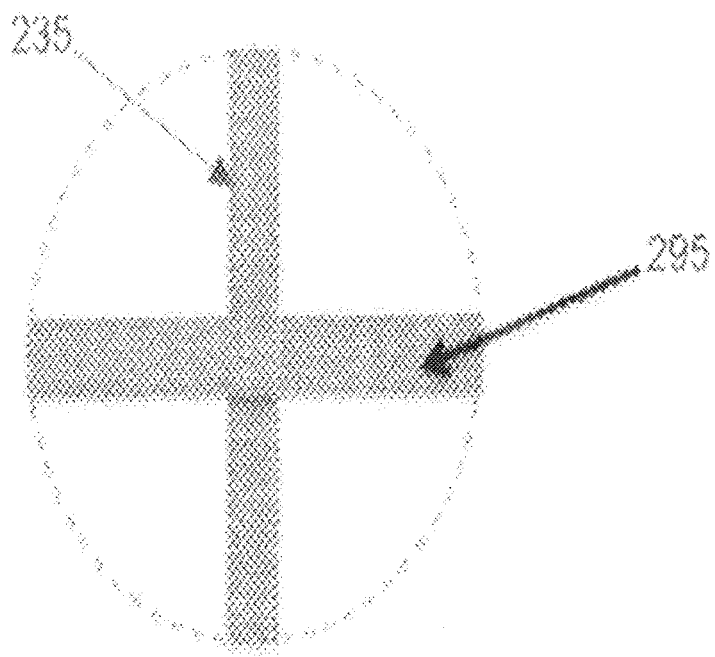
FIGS. 62 and 63 are diagrammatic illustrations of occluders with legs of different lengths and defining an oval region of compression.
Figure 63:
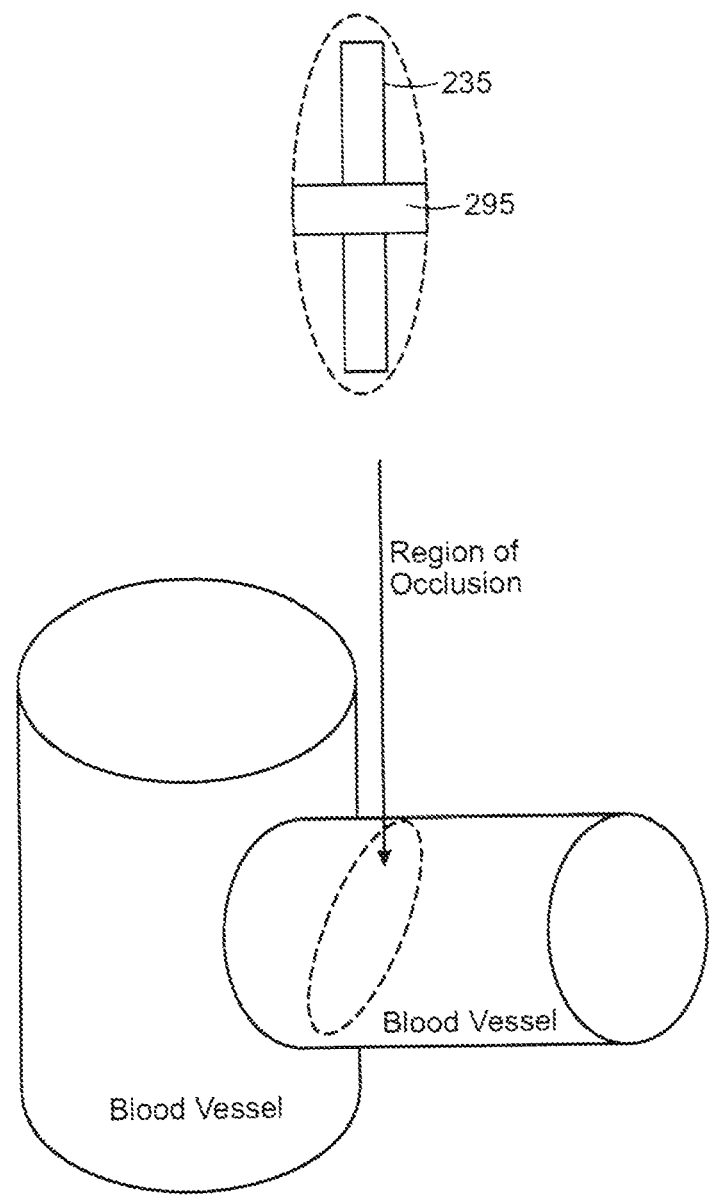

In one form of the present invention, the pressure zone (the area in which the tissue layers are urged into contact) generated by two-part occluder 200 is a generally circular area extending around the entry point of the transfixing distal locking tube 220 (FIG. 62), but in other embodiments the pressure zone may be non-circular, meaning that the lengths of legs 235 of distal implant 205 and legs 295 of proximal implant 210 are not equal. For example, an oval pressure zone may be employed with legs of unequal or asymmetric length, so that the occluder 200 can be positioned proximal to a branched vessel or tissue, as shown in FIG. 63. In one form of the present invention, the orientation of the proximal and distal implants of two-part occluder 200 can be determined using markings disposed on the delivery device handle (e.g., an arrow which indicates the long direction of legs 235, 295). In laparoscopic or open procedures, the orientation of two-part occluder 200 can also be visually confirmed. In percutaneous applications, ultrasound, or CT imaging can be used to further determine orientation of two-part occluder 200 relative to vessels, ducts, organs, tissue that is are to be clamped or occluded.

FIGS. 64-72 illustrate the components of a modified occluder having a locking mechanism of tangs and windows that assures locking of the implants when they are brought together, regardless of their orientation. In this arrangement the distal implant can be laser cut with one or more windows circumferentially spaced about the hollow tubular section of the implant. The mating proximal implant can be cut to include one or more tangs, each tang configured to engage a window, thereby locking the two occlusion elements together. In the embodiment of FIGS. 64-72, the tangs and windows are designed to lock together regardless of the angular orientation of the legs of the implants (a feature referred to as "angular relation indifference."

Figure 64:
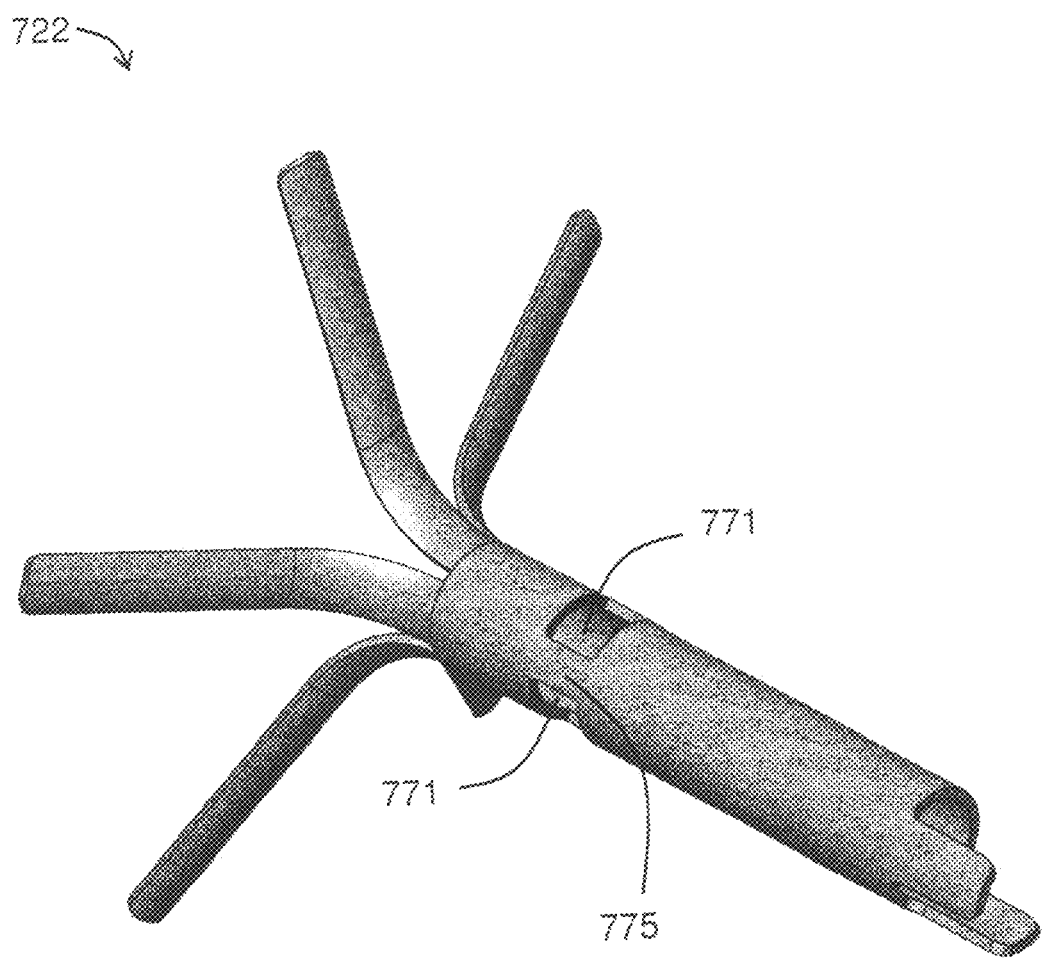
FIG. 64 is an illustration of a distal implant with a plurality of circumferentially spaced tang-receptive windows of a modified locking arrangement.

FIG. 64 shows a distal implant 722 with three windows 771 (only two visible) that are spaced evenly around the circumference of the occlusion element 722, located proximal to the legs. A portion 775 of the tube separates and frames each pair of adjacent windows 771. In the embodiment shown, each of the three windows 771 occupies approximately 80 degrees of the circumference of the tube, and each window frame portion 775 occupies approximately 40 degrees of the circumference of the tube. It should be understood that other arrangements and sizes of windows are possible that will still achieve the angular relation indifference configuration.

Figure 65:
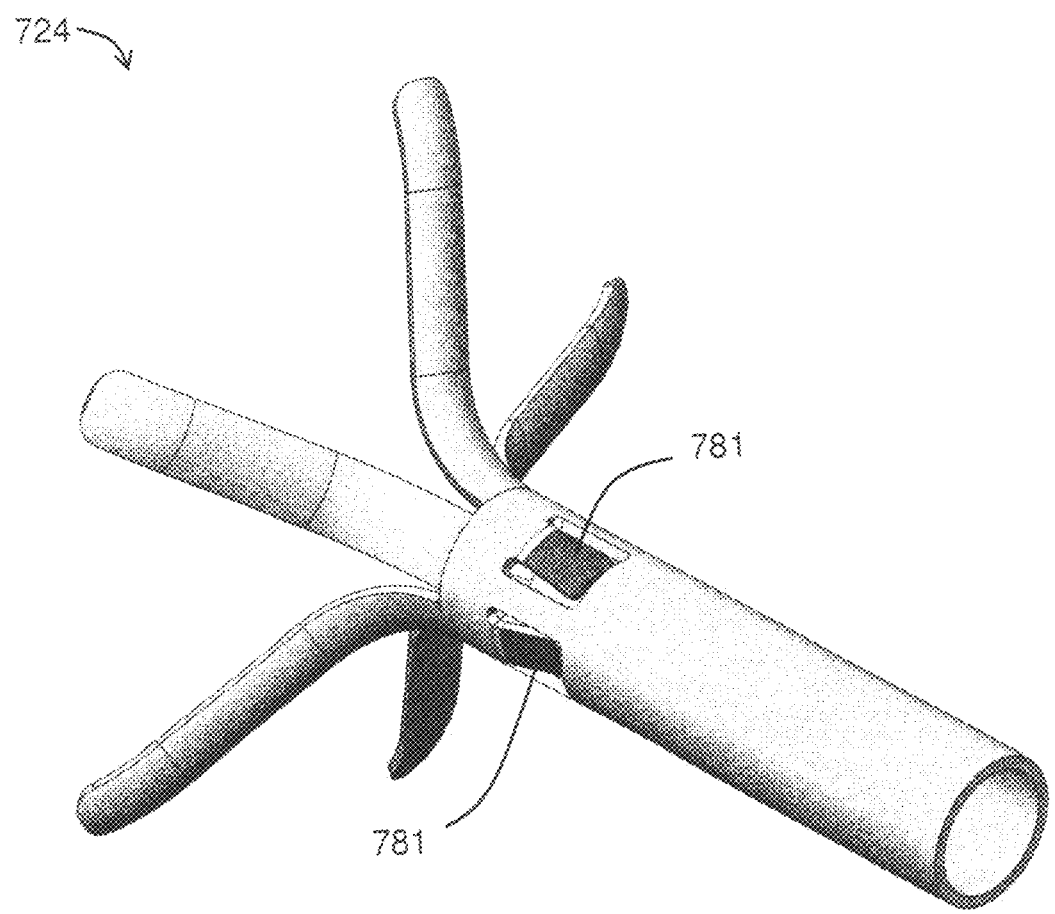
FIG. 65 is an illustration of a proximal implant with a plurality of circumferentially spaced window-engageable tangs of a modified locking arrangement.
Figure 66:
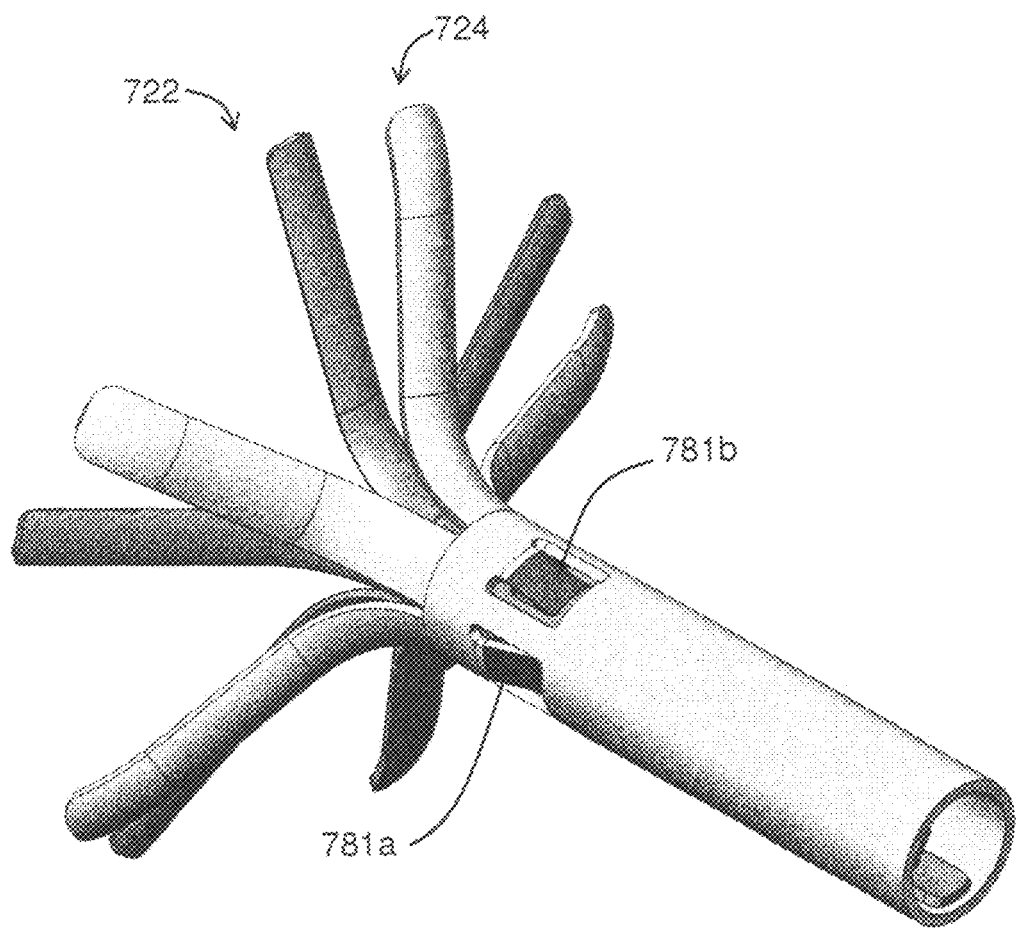
FIG. 66 is an illustration of the proximal and distal implants of FIGS. 65 and 66 locked together.
Figure 67:
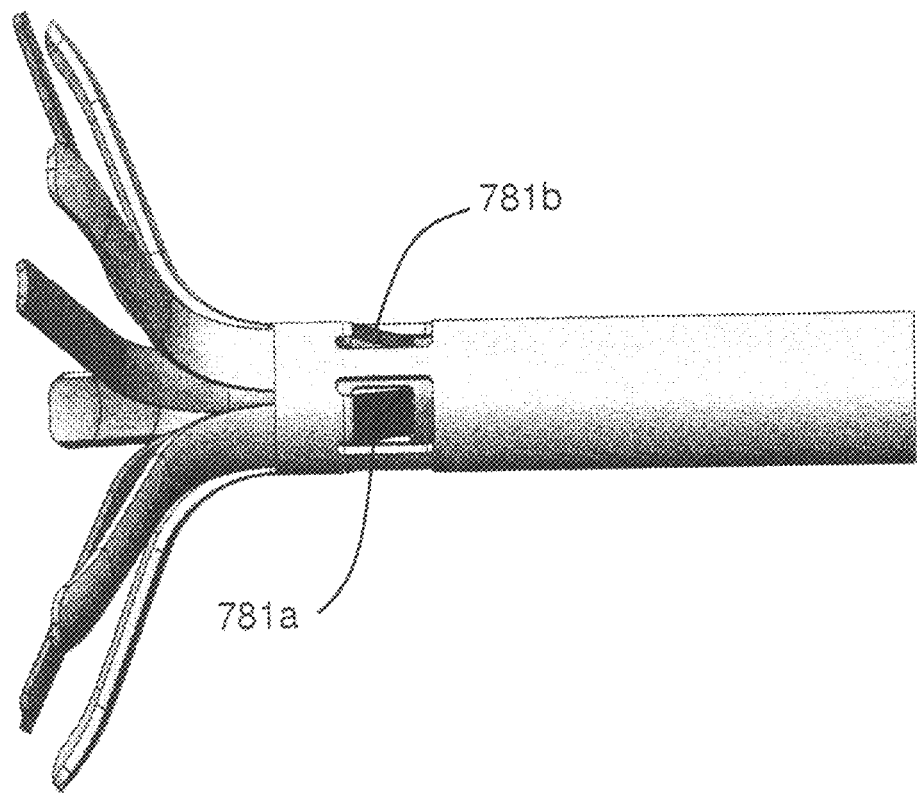
FIG. 67 is another view of the engaged implants of FIG. 67.

FIG. 65 shows a proximal implant 724 with four inwardly projecting tangs 781, only two of which are visible in the drawing. Despite the different numbers of windows 771 and tangs 781, FIGS. 66-72 illustrate how the distal implant 722 and the proximal occlusion element 724 will lock together, regardless of their angular orientation. FIG. 66 shows the proximal implant 724 and the distal implant 722 locked together. The distal implant 722 has a smaller diameter than the proximal implant 724 and fits within the hollow tube of the proximal implant 724. The two visible tangs 781a and 781b are both projecting inwardly into the corresponding windows 771 of the distal implant 722, thereby locking them in place. FIG. 67 shows a side view to more clearly show the inwardly projecting tangs 781a and 781b locked in place with respect to the windows 771.

Figure 68:
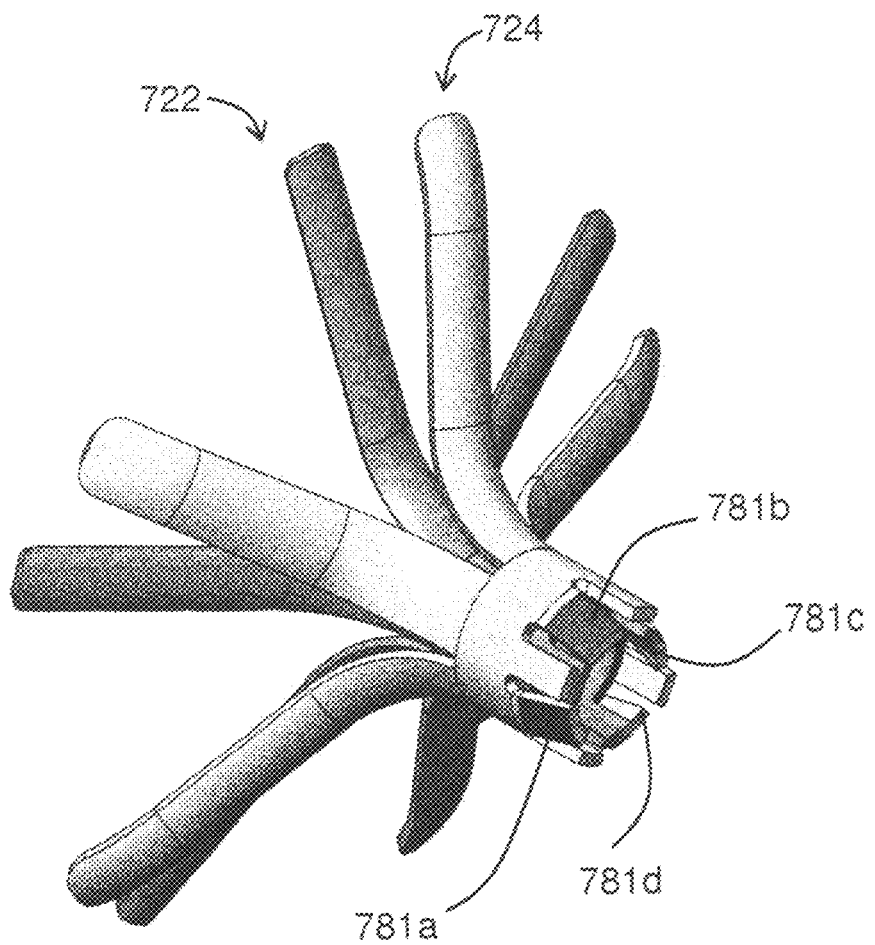
FIG. 68 is a cut-away illustration of the engaged implants of FIGS. 65 and 66.

FIG. 68 shows a sectioned view of the two implants locked together. Due to the different configurations of the tangs 781 and windows 771 (i.e., there are four tangs 781a-d but only three windows 771a-c), tangs 781c and 781d do not project into the windows 771 in the orientation shown. However, regardless of orientation of the two occlusion elements, at least one (and as many as two) of the four tangs will always be locked in place. That angular relation indifference is shown more clearly in FIGS. 70-72.

Figure 69:
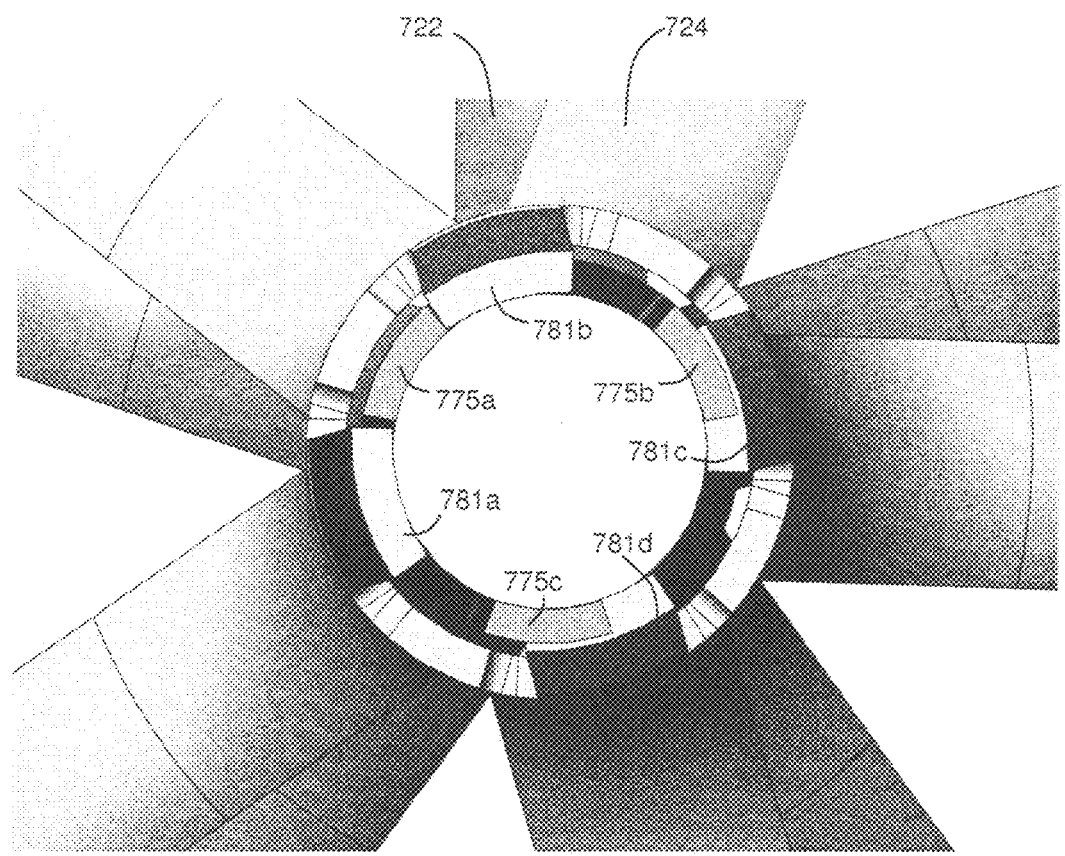

FIG. 69 shows a close-up cross-section view of the two implants locked together. In this orientation, tang 781a is locked in place in the window 771 defined by window frame elements 775a and 775b; and tang 781b is locked in place in the window 771 defined by window frame elements 775a and 775c. Tangs 781c and 781d are not projecting into windows, but are instead contacting window frame elements 775b and 775c, respectively. FIG. 70 shows a slightly different orientation between the two elements. This orientation is rotated clockwise from the orientation shown in FIG. 70. In FIG. 70, tangs 781b and 781c project into windows 771 framed by elements 775a and 775b, and 775b and 775c, respectively. Tangs 781a and 781d are in contact with window frame elements 775a and 775c, respectively. FIGS. 71 and 72 show two other orientations, with the proximal occlusion element 724 rotated clockwise with respect to the preceding orientation. Regardless of how many degrees the proximal occlusion element 724 is offset from the distal occlusion element 722 (from 0-360 degrees), in any orientation there will always be at least one, and as many as two, of the tangs locked into one of the windows, due to the angular relation indifference configuration.

The tangs and windows may be configured to control the relative angular position of the legs of the proximal and distal implants. For example, the windows and tangs may be configured to engage only when the legs of the two implants are oriented in a specific angular relation. Thus, the legs of a distal occluder can be offset with respect to those of the proximal occluder to achieve an interdigitating configuration as discussed above. In other embodiments, it may be desirable for the legs to align so as to compress the structure between aligned legs. Other alignments may be preferable as well, including partially offset legs.

Figure 78:
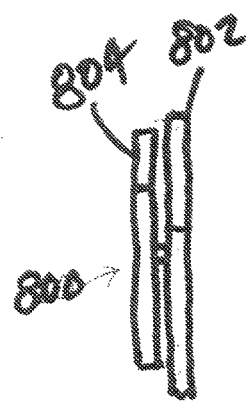
FIGS. 78-80 illustrate another embodiment of the invention.
Figure 79:
Figure 80:
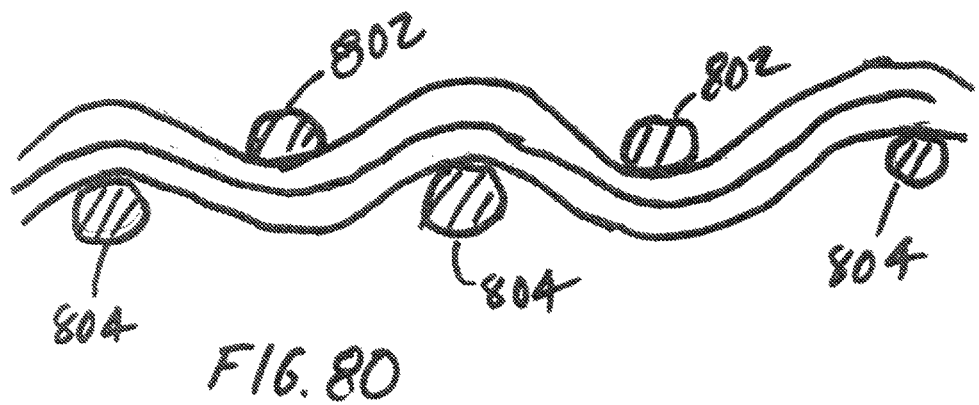

FIGS. 78-80 illustrate, diagrammatically, another type of occluder 800 that may be formed from a wire of shape memory material, such as Nitinol and constrains the tissues in a serpentine pattern. The wire can be delivered through a needle or other delivery tube that is first advanced through the walls of the vessel or tissue layers, as described below. The wire may be maintained in a linear configuration by the lumen of the needle or delivery tube but reverts to its preformed "memorized" shape as it advances out of the needle. As shown in FIGS. 78 and 79 the occluder, when fully released has a shape memory of a pair of spaced spiral coils 802, 804 connected by an intermediate transluminal segment 806. The spirals are generally similar and parallel each other except that the wire of one of the spirals overlies the spaces defined by the other spiral as shown, diagrammatically in FIG. 79. The transluminal segment 806 connects the inner most ends of the spirals 802, 804. It is relatively short to be able to span and extend through the compressed tissue and to space the spirals so that they engage the outer surfaces of the tissue and constrain the tissues in a serpentine pattern as illustrated in FIG. 80. The serpentine pattern is considered to effectively secure the tissue layers together with less force than is applied with a more conventional clamp. In the case of a blood vessel or other tubular body organ the occluder may be effective to occlude flow of blood or other fluid through the vessel. The device is delivered by first transfixing the vessel or tissue layers with the needle of delivery tube. Then, the distal portion of the wire is advanced out of the distal end of the needle or tube. Freed from its restraint, the distal portion of the wire self expands to the desired shape of the distal spiral. The needle or tube then is withdrawn to locate its distal tip on the proximal side of the vessel or tissue and then the proximal portion of the wire is released to form the proximal spiral, the transluminal portion extending transversely through the tissue. The wire composition and dimensions may be varied to suit varying anatomical considerations as will be appreciated by those skilled in the art.

In each of the foregoing embodiments the transfixion aperture that is formed by the device does not tend to leak blood (or other fluid) because the zone about the point of transfixion where the legs cooperate to prevent fluid flow substantially prevents fluid from reaching the aperture. Thus, the invention may be advantageous in many situations over other techniques in which blood loss may be problematic (e.g., staples, sutures, etc.)

Thus, it will be appreciated that the foregoing description provides devices and methods for occluding vessels and for clamping tissue layers that provide advantages over prior art techniques. Occluders and clamps are provided that employ a pair of components that are brought together on opposite sides of a vessel or tissue layers to compress the vessel walls or tissue layers. The clamping may be directly on the tissue or may be such as to constrain the tissue layers in a serpentine pattern that is considered to occlude or clamp with less direct compressive force on the tissue. Applying oppositely directed forces at alternating locations on the tissue circumferentially about the center of the occluder also may effect occlusion or clamping. The occluders may include pluralities of radially extending legs or spirally oriented elements that cooperate to effect occlusion or clamping. In each instance a pressure zone of occlusion is formed about the point of transfixion to prevent leakage through the transfixion aperture.

It should be understood, however, that the foregoing description of the invention is intended merely to be illustrative and that other embodiments, modification and equivalents may be apparent to those skilled in the art without departing from the principles of the invention.

The invention claimed is:

1. A method for clamping tissue layers together, each layer, prior to clamping, having an inwardly facing surface and an outwardly facing surface, the method comprising:
    constraining the tissue layers together by applying oppositely directed forces to the outwardly facing surfaces of the tissue layers to urge the inwardly facing surfaces together, the forces being applied alternately at circumferentially spaced locations about a central location to constrain the tissue layers in a serpentine configuration that circumscribes the central location.

2. The method as defined in claim 1 wherein the tissue layers comprise the walls of a tubular or hollow anatomical structure.

3. The method as defined in claim 1 further comprising:
    providing a first clamping member;
    providing a second clamping member separate from the first clamping member;
    deploying the first clamping member opposite and facing the outwardly facing surface of one of the layers;
    thereafter deploying the second clamping member opposite and facing the outwardly facing surface of the other of the layers; and
    drawing the first and second clamping members toward each other to apply the oppositely directed, circumferentially spaced forces to the layers.

4. The method as defined in claim 1 further comprising:
    the tissue layers being naturally opposed with the inwardly facing surfaces facing each other;
    the forces being applied in directions that are approximately perpendicular to the tissue layers.

5. The method as defined in claim 4 wherein the tissue layers comprise opposing walls of a tubular anatomical structure.

6. The method as defined in claim 1 further comprising:
    forming an opening through the layers;
    passing a distal clamping member through the opening to locate the distal clamping member distally of the layers;
    locating a proximal clamping member proximally of the layers; and
    drawing the proximal and distal clamping members together to constrain the layers.

7. A method for clamping tissue layers together, the layers comprising opposing portions of a tubular or hollow anatomical structure and where the clamping at least partially occludes the lumen of the anatomical structure, each layer, prior to clamping, having an inwardly facing layer and an outwardly facing layer, the method comprising:
    constraining the tissue layers together by engagement with their outwardly facing surfaces to urge the inwardly facing surfaces together in a serpentine configuration and having at least three sequentially reversing bends, the serpentine configuration circumscribing an axis that is approximately perpendicular to the tissue layers.

8. The method as defined in claim 7 wherein the tissue layers comprise the walls of a tubular or hollow anatomical structure.

9. The method as defined in claim 7 further comprising:
    providing a first clamping member;
    providing a second clamping member separate from the first clamping member;
    deploying the first clamping member opposite and facing the outwardly facing surface of one of the layers;
    thereafter deploying the second clamping member opposite and facing the outwardly facing surface of the other of the layers; and
    drawing the first and second clamping members toward each other to constrain the layers in a serpentine configuration having at least three sequentially reversing bends.

10. The method as defined in claim 7 further comprising:
    forming an opening through the layers;
    passing a distal clamping member through the opening to locate the distal clamping member distally of the layers;
    locating a proximal clamping member proximally of the layers; and
    drawing the proximal and distal clamping members together to constrain the layers.

11. A method for clamping together a tissue layer to another tissue or non-tissue layer, each layer, prior to clamping, having an inwardly facing surface and an outwardly facing surface, the method comprising:
  with the inwardly facing surfaces facing each other, constraining the layers together by applying oppositely directed forces to the outwardly facing surfaces of the layers, the forces being applied alternately at circumferentially spaced locations about a central location to form the layers into a serpentine configuration that circumscribes the central location.

12. The method as defined in claim 11 further comprising:
  forming an opening through the layers;
  passing a distal clamping member through the opening to locate the distal clamping member distally of the layers;
  locating a proximal clamping member proximally of the layers; and
  drawing the proximal and distal clamping members together to constrain the layers.

13. A method for clamping a tissue layer to another tissue or non-tissue layer, each layer, prior to clamping, having an inwardly facing layer and an outwardly facing layer, the method comprising:
  constraining the layers together by engagement with their outwardly facing surfaces to urge the inwardly facing surfaces together in a serpentine configuration and having at least three sequentially reversing bends, the serpentine configuration circumscribing an axis that is approximately perpendicular to the tissue layers.

* * * * *